US010100011B2

(12) United States Patent
Park et al.

(10) Patent No.: US 10,100,011 B2
(45) Date of Patent: Oct. 16, 2018

(54) PENTADIENOYL PIPERIDINE DERIVATIVE AND USE THEREOF

(71) Applicants: Industry-Academic Cooperation Foundation, Yonsei University, Seoul (KR); SNU R&DB Foundation, Seoul (KR)

(72) Inventors: Tae Sun Park, Seoul (KR); Lak Shin Jeong, Seoul (KR)

(73) Assignees: INDUSTRY-ACADEMIC COOPERATION FOUNDATION, YONSEI UNIVERSITY, Seoul (KR); SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 15/513,072

(22) PCT Filed: Sep. 22, 2015

(86) PCT No.: PCT/KR2015/009944
§ 371 (c)(1),
(2) Date: Mar. 21, 2017

(87) PCT Pub. No.: WO2016/048005
PCT Pub. Date: Mar. 31, 2016

(65) Prior Publication Data
US 2017/0320825 A1    Nov. 9, 2017

(30) Foreign Application Priority Data

Sep. 23, 2014  (KR) .................... 10-2014-0126959

(51) Int. Cl.
*C07D 211/32* (2006.01)
*A61K 31/4453* (2006.01)
*C07C 225/16* (2006.01)

(52) U.S. Cl.
CPC ........ *C07D 211/32* (2013.01); *A61K 31/4453* (2013.01); *C07C 225/16* (2013.01); *A61K 2300/00* (2013.01)

(58) Field of Classification Search
CPC .. C07D 211/32; A61K 31/4453; C07C 225/16
(Continued)

(56) References Cited

U.S. PATENT DOCUMENTS

2004/0121994 A1   6/2004   Anderson et al. ............ 514/183
2007/0142394 A1   6/2007   Solomon et al. ........ 514/253.01

FOREIGN PATENT DOCUMENTS

WO    WO 2005019177    3/2005
WO    WO 2006068075    6/2006
WO    WO 2009004071    1/2009

OTHER PUBLICATIONS

Bligh, E.G., and W. J. Dyer. "A rapid method for total lipid extraction and purification." *Canadian Journal of Biochemistry and Physiology* 37.8 (1959):911-917.
(Continued)

*Primary Examiner* — Rita J Desai
(74) *Attorney, Agent, or Firm* — Norton Rose Fulbright US LLP

(57) ABSTRACT

The present invention relates to a novel pentadienoyl piperidine derivative, a pharmaceutical composition containing the same for prevention or treatment of metabolic diseases, and a functional food composition using the same for improvement or relief of metabolic diseases. The pentadienoyl piperidine derivative of the present invention inhibits the differentiation of preadipocytes, reduces body weight, visceral fat, blood lipid levels, and blood glucose levels, improves a blood liver function index, and suppresses metabolic inflammation responses. Thus, ultimately, the derivative can be usefully used as a medicine or a functional food composition, which exhibits the preventive or therapeutic
(Continued)

activity for metabolic diseases selected from the group consisting of obesity, diabetes, dyslipidemia, fatty liver and insulin resistance syndrome.

11 Claims, 25 Drawing Sheets

(58) Field of Classification Search
USPC .......................................... 546/226; 514/317
See application file for complete search history.

(56) References Cited

OTHER PUBLICATIONS

Folch, Jordi, M. Lees, and G. H. Sloane-Stanley. "A simple method for the isolation and purification of total lipids from animal tissues." *J biol Chem* 226.1 (1957): 497-509.
Freeman, Bruce A., and J. D. Crapo. "Biology of Disease: Free Radicals and Tissue Injury." *Laboratory Investigation* 47.5 (1982):412-426.
Kawamura, Mitusnobu, J. W. Heinecke, and A. Chait. "Pathophysiological concentrations of glucose promote oxidative modification of low density lipoprotein by a superoxide-dependent pathway." *J. Clin. Invest.* 94 (1994):771-778.
Nelson, Gary J. "Isolation and purification of lipids from animal tissues." *Analysis of Lipids & Lipoproteins. EG Perkins, ed* (1975).
Reaven, Gerald M. "Banting lecture 1988: Role of insulin resistance in human disease." *Diabetes* 37 (1988):1595-1607.

PENTADIENOYL PIPERIDINE DERIVATIVE AND USE THEREOF

CROSS-REFERENCE TO RELATED APPLICATIONS

This application is a national phase application under 35 U.S.C. § 371 of International Application No. PCT/KR2015/009944 filed Sep. 22, 2015, which claims priority to Korean Patent Application No. 10-2014-0126959 filed Sep. 23, 2014. The contents of each of the above-referenced applications are incorporated into the present application by reference.

TECHNICAL FIELD

The present invention was supported by grants from the Ministry for Food, Agriculture, Forestry and Fisheries (MI-FAFF) (No. 1130373) and the Ministry of Education, Science and Technology (MEST) (No. 2015R1A5A6001906). The specialized agency of R&D management with regard to the grant number, 1130373, is the Korea Institute of Planning and Evaluation for Technology in Food, Agriculture Forestry and Fisheries (iPET), the title of the research program is "Technology Commercialization Supporting Program", the title of the research project is "Individual-authorized health functional food materials for body weight control and improvement of metabolic diseases using extract from Artemisia iwayomogi", the lead agency is the Industry-Academic Cooperation Foundation of Yonsei University, and the project period is Nov. 27, 2013 to Oct. 26, 2014. The specialized agency of R&D management with regard to the grant number, 2015R1A5A6001906, is the National Research Foundation of Korea (NRF), the title of the research program is "Advanced Research Center Program SRC (Science Research Center)", the title of the research project is "Research Center for Food and Nutritional Genomics", the lead agency is the Industry-Academic Cooperation Foundation of Kyungpook National University, and the project period is Mar. 1, 2013 to Feb. 28, 2014. The present patent application claims priority to Korean Patent Application No. 10-2014-0126959 filed with the Korea Intellectual Property Office on Sep. 23, 2014, and the disclosure of the patent application is incorporated by reference herein. The present invention relates to a novel pentadienoyl piperidine derivative and a composition containing the same for preventing or treating metabolic disease.

BACKGROUND ART

The onset of metabolic syndromes, accompanying diabetes, hypertension, disorders of lipid metabolism, insulin resistance, etc., is rapidly increasing while intra-abdominal fat accumulated obesity increases in modern people due to changes in a living environment. The diseases mutually affect each other, increasing the risk of their occurrence, and are common diseases, which are related with in vivo metabolic changes caused by diverse factors, such as aging, stress and a decline in immune function, etc. Obesity can cause chronic diseases, such as fatty liver, hypertension, diabetes, cardiovascular disease, etc., as well as a physical appearance problem.

At present, 1.7 billion people, equivalent to about 25% of world population, are overweight (BMI>25), and more than 300 million people, including 120 million people in the United States, Europe, and Japan as major markets, are classified as obese (BMI>30) in the West. The United States, where 31% of the entire nation are obese, has the highest rate of obesity among OECD countries, followed by Mexico (24%), the United Kingdom (23%), Greece (22%), Australia (22%), New Zealand (21%), Hungary (19%), Canada (14%), Spain (13%), Ireland (13%), Germany (13%), Portugal (13%), Finland (13%), Turkey (12%), and Belgium (12%). In China, the obese population numbers 70 million, markets relating to body weight control have been rapidly growing, and the total size of the markets is expected to reach about 10 billion yuan. In addition, one in five children in the world are currently affected by childhood obesity, which has emerged as a serious social problem due to a high incidence of the disease. Childhood obesity may be a major cause of diabetes, hypertension, stroke, etc., called 'lifestyle related diseases', due to high levels of blood cholesterol and neutral fat, and 80% or more of obese children graduate to adult obesity, leading to serious health problems. Furthermore, puberty may come early for one's age, since excessive fat accumulation stimulates secretion of sex hormones, which may cause growth disorders. Additionally, childhood obesity affects blood circulation and nutrient supply, which may also cause impaired growth.

Non-alcoholic fatty liver disease (NAFLD) refers to a disease, in which neutral fat is accumulated in the liver regardless of drinking, and includes steatosis and non-alcoholic steatohepatitis (NASH). Whereas steatosis is clinically considered a benign disease, NASH as a progressive liver disease, which accompanies inflammation or fibrosis with fatty liver, is considered as a pre-symptomatic disease that causes liver cirrhosis or liver cancer.

Obesity and insulin resistance are representative risk factors for non-alcoholic fatty liver disease. For example, risk factors for hepatic fibrosis progression are obesity (BMI>30), the ratio of liver-function indicators in the blood (AST/ALT>1) and diabetes. Particularly, hepatitis C may proceed into liver cancer in people with hepatitis C who suffer from non-alcoholic fatty liver (NAFL), and thus a need for prevention and treatment of the diseases has emerged as an important issue. 69-100% of non-alcoholic fatty liver patients are obese patients, and 20-40% of obese patients have non-alcoholic fatty liver. Particularly, the prevalence of liver diseases is higher in obese men than in obese women. It has been reported that lesions of non-alcoholic fatty liver appear in 3-30% of adults with normal body weight, as well as obese patients, in Western society. The prevalence of non-alcoholic fatty liver is estimated to be about 20% in Japan, where a dietary life is similar to ours, and 1% of the 20% is estimated to have NASH. Non-alcoholic fatty liver is a problem in obese children as well as adults. 10-77% of obese children (living in Europe, the United States and Asia) show lesions of non-alcoholic fatty liver, which supports the fact that obesity is the most important risk factor for non-alcoholic liver disease.

Anti-obesity drugs, which are sold domestically and abroad, include Xenical (Roche Korea Co., Ltd.), a main component of which is orlistat approved by the U.S. FDA, Reductil (Ilsung Pharm. Co., Ltd.), of which sibutramine is a component, and Exolise (Guju Pharm. Co., Ltd.), which has a catechol ingredient of green tea as a component. Xenical, which inhibits lipase functionality, has side effects on the gastrointestinal system, such as fatty stools, gas generation, reduced absorption of fat-soluble vitamins, etc., and Reductil, which increases the concentrations of serotonin and noradrenalin in the sympathetic nervous system, has side effects, such as headaches, thirst, anorexia, insomnia, constipation, etc. Sales of a considerable number of drugs, which have been developed for anti-obesity, have been prohibited due to serious side effects. For example, aminophylline has been reported to have wide-ranging side effects on the nervous system, circulatory system, and digestive system in spite of its excellent effect of breaking down body fat. Additionally, several drugs, including fenfluramine, dexfenfluramine, topiramate, ephedrine, etc., were not approved as appropriate drugs for obesity treatment, and thus sales thereof was prohibited. Thus, as conventional synthetic drugs have shown limits owing to their side effects, the demand for novel drug compositions for obesity treatment, which are adequate for treatment of chronic diseases by virtue of their safety for long-term use, is increasing.

A number of papers and other patent documents are referenced throughout the present specification, and the citations are marked in the specification. Disclosures of the cited papers and other patent documents are incorporated by references herein in their entirety, whereby level of a technical field pertaining to the present invention and contents of the present invention are clearly explained.

DISCLOSURE

Technical Problem

The present inventors have tried to develop a compound, which has an activity of prevention or treatment of metabolic diseases, including obesity, diabetes, dyslipidemia, fatty liver and insulin resistance syndrome, etc. As a result, a novel pentadienoyl piperidine derivative, which has the structure of Formula 1, has been demonstrated to reduce body fat and blood glucose, and greatly improve various indices of metabolic diseases, whereby the derivative has an effect of preventing and treating lipid metabolic diseases. By finding the above, the present invention was completed.

Accordingly, an objective of the present invention is to provide the pentadienoyl piperidine derivative or a pharmaceutically acceptable salt thereof.

Another objective of the present invention is to provide a pharmaceutical composition for prevention or treatment of metabolic diseases selected from the group consisting of obesity, diabetes, dyslipidemia, fatty liver and insulin resistance syndrome.

Another objective of the present invention is to provide a food composition for improvement or relief of metabolic diseases selected from the group consisting of obesity, diabetes, dyslipidemia, fatty liver and insulin resistance syndrome.

Another objective of the present invention is to provide a method for prevention, improvement or treatment of metabolic diseases selected from the group consisting of obesity, diabetes, dyslipidemia, fatty liver and insulin resistance syndrome.

Other objective and benefits of the present invention are clearly defined in detailed description, claims, and drawings of the invention, as described below.

Technical Solution

According to one aspect of the present invention, the present invention provides a pentadienoyl piperidine derivative represented by Formula 1 below or a pharmaceutically acceptable salt thereof:

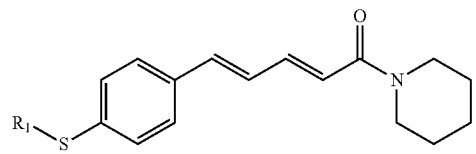

Formula 1 wherein R1 is a $C_1$-$C_3$ alkyl group.

The present inventors have tried to develop a compound, which has activity toward prevention or treatment of metabolic diseases, including obesity, diabetes, dyslipidemia, fatty liver and insulin resistance syndrome, etc. As a result, the novel pentadienoyl piperidine derivative, which has the structure of Formula 1, has been demonstrated to reduce body fat and blood glucose, and greatly improve various indices of metabolic diseases, whereby the derivative has an effect of preventing and treating lipid metabolic diseases.

In the specification of the present invention, the term "alkyl" refers to a linear or branched saturated hydrocarbon radical and, for example, includes methyl, ethyl, propyl, isopropyl, etc. The $C_1$-$C_3$ alkyl refers to an alkyl group that has an alkyl unit with 1 to 3 carbons. The carbon number of the substituent is not included when the $C_1$-$C_3$ alkyl is substituted.

According to an embodiment of the present invention, $R_1$ of Formula 1 is a methyl group.

The IUPAC nomenclature for a compound of Formula 1 with a methyl group as $R_1$ is "(2E,4E)-5-(4-(methylthio)phenyl)-1-(piperine-1-yl)penta-2,4-diene-1-one." As described in the following examples, the compound of the present invention was confirmed to have a superior anti-obesity effect compared to other compounds with a similar backbone, which has a different substituent (alkylthio) and substitution position (meta) of the phenyl group.

The compound of the present invention may be used in the form of a pharmaceutically acceptable salt. Acid-addition salts, which are formed by pharmaceutically acceptable free acids, are applicable salts. Inorganic acids and organic acids may be used as free acids.

Specifically, the pharmaceutically acceptable salt of the compound of the present invention may be selected from the group consisting of hydrochloride, bromate, sulfate, phosphate, citrate, acetate, trifluoroacetate, lactate, tartrate, maleate, fumarate, gluconate, methanesulfonic acid, gluconate, succinate, 4-toluenesulfonate, glucuronate, embonate, glatamate, or aspartate, but are not limited thereto, and include any salt formed by using various inorganic acids and organic acids, which are commonly used in the art. Additionally, the compound of the present invention may exist in a form of a solvate (for example, a hydrate).

According to another aspect of the present invention, the present invention provides a pharmaceutical composition, wherein the pentadienoyl piperidine derivative or the pharmaceutically acceptable salt thereof of the present invention is contained as an active ingredient for prevention or treatment of metabolic diseases selected from the group consisting of obesity, diabetes, dyslipidemia, fatty liver and insulin resistance syndrome.

According to the present invention, the compound of the present invention was confirmed to inhibit the differentiation of preadipocytes, and reduce body weight, visceral fat, and blood lipid levels, and to improve a blood liver function index, and suppress metabolic inflammation responses while reducing blood glucose levels. Thus, the compound of the present invention may be used as a compound for prevention or treatment of various metabolic diseases.

As used herein, the term "diabetes" refers to a chronic disease characterized by relative or absolute insulin deficiency, which causes glucose-intolerance. Diabetes according to the present invention includes all types of diabetes, for example, type 1 diabetes, type 2 diabetes, and hereditary diabetes. Type 1 diabetes (also known as insulin dependent diabetes) is primarily caused by destruction of β-cells, whereas type 2 diabetes (also known as insulin independent diabetes) is caused by insufficient secretion of insulin after eating or by insulin resistance.

As used herein, the term "dyslipidemia", as a concept including hyperlipidemia, refers to an abnormal lipid status derived by a metabolic disorder of lipoproteins as well as hypercholesterolemia, hypertriglyceridemia, and hypo HDL-cholesterolemia caused by an increase of blood lipids.

As used herein, the term "fatty liver" refers to a state, wherein excessive fat is accumulated in the liver by lipid metabolism disorders of the liver, and may trigger various diseases, such as angina pectoris, myocardial infarction, stroke, arteriosclerosis, fatty liver, pancreatitis, etc.

As used herein, the term "insulin resistance" refers to a state, wherein glucose is not effectively consumed by cells owing to reduction of insulin action responsible for lowering blood glucose. High insulin resistance causes the excessive production of insulin, by which even heart diseases and diabetes as well as hypertension or dyslipidemia may be triggered. Particularly, in type 2 diabetes, insulin action does not occur because increased levels of insulin are not recognized in the muscle and adipose tissues.

As used herein, the term "insulin resistance syndrome", as a general concept for diseases induced by the insulin resistance, refers to a disease characterized by resistance of cells to insulin action, hyperinsulinemia, an increase of a very low density lipoprotein (VLDL) and neutral fat, a decrease of a high density lipoprotein (HDL), and hypertension, etc., and is considered as a risk factor for cardiovascular diseases and type 2 diabetes (Reaven G M, Diabetes, 37: 1595-607, 1988). Additionally, insulin resistance has been known to facilitate progression of atherosclerosis through an inflammatory reaction, which is induced by altered signaling pathways and increased intracellular oxidation stress along with the risk factors, such as hypertension, diabetes and smoking, etc. (Freeman B A et al, Lab Invest 47: 412-26, 1982 and Kawamura M et al, J Clin Invest 94: 771-8, 1994).

As used herein, the term "metabolic disease", as a comprehensive concept, which combines multiple disease symptoms caused by risk factors for various cardiovascular disorders and type 2 diabetes into one disease group, includes insulin resistance and related metabolic disorders and clinical aspects with complexity and diversity. Although Reaven named the metabolic disease "insulin resistance syndrome" in 1988 based on his insistence that a common cause of the symptoms is insulin resistance, by which insulin does not effectively act in the body, the WHO introduced the term, "metabolic syndrome or metabolic disease", in 1998 because all of the components of the symptoms may not be fully explained by insulin resistance alone.

As used herein, the term, "treatment" refers to (a) suppressing the progress of illnesses, diseases or symptoms; (b) relief of illnesses, diseases or symptoms; or (c) removal of illnesses, diseases or symptoms. The composition of the present invention has a role in suppressing the development of metabolic disease symptoms, or removing or relieving the same. Accordingly, the composition of the present invention itself may be a composition for the treatment of a metabolic disease, or the composition may be applied as an adjuvant, which is administrated together with a composition for the treatment of other metabolic diseases. Thus, in the specification of the present invention, the term "treatment" or "medicine" includes the meaning of "treatment assistance" or "adjuvant".

According to an embodiment of the present invention, the dyslipidemia to be treated and prevented by the composition of the present invention is hyperlipidemia.

As used herein, the term "hyperlipidemia" refers to a disease, which causes a high fat content in the blood owing to impaired lipid metabolism for neutral fat and cholesterols, etc. More specifically, hyperlipidemia includes hypercholesterolemia or hypertriglyceridemia, which frequently occurs when lipid components, such as neutral fat, LDL cholesterol, phospholipids and free fatty acids, increase in the blood.

According to an embodiment of the present invention, the fatty liver to be treated and prevented by the composition of the present invention is non-alcoholic fatty liver.

In the specification of the present invention, the term "non-alcoholic fatty liver (Non-alcoholic fatty liver, NAFL)" refers to a disease, in which excessive fat is accumulated in the liver cells regardless of excessive absorption of alcohol.

According to an embodiment of the present invention, the composition of the present invention reduces the differentiation of adipocytes. More specifically, the composition of the present invention reduces blood fat, liver fat or visceral fat. Still more specifically, the visceral fat includes one or more types of fat selected from epididymal fat, perirenal fat, mesenteric fat and retroperitoneal fat.

In the present invention, the terms "liver" and "viscus" include cells and tissue, respectively.

According to an embodiment of the present invention, the composition of the present invention reduces the activity of alanine aminotransferase (ALT) or aspartate aminotransferase (AST) in the blood.

According to the present invention, the composition of the present invention significantly reduced the amounts of ALT and AST (60-65%, respectively) in the blood compared to a high-fat diet control group, and thus the composition was confirmed to have an effect of improving fatty liver through relieving the symptoms of fatty liver, more specifically, non-alcoholic fatty liver.

When the composition of the present invention is prepared as a pharmaceutical composition, the pharmaceutical composition of the present invention contains pharmaceutically acceptable carriers. The pharmaceutically acceptable carriers contained in the pharmaceutical composition of the present invention include, as components generally used when producing pharmaceutical compositions, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, stearic acid magnesium and mineral oil, etc., but are not limited thereto. The pharmaceutical composition of the present invention may additionally contain lubricants, humectants, sweetening agents, flavoring agents, emulsifying agents, suspensions, preserved agents, and so forth besides the components described above. Proper pharmaceutically acceptable carriers and preparations are described in *Remington's Pharmaceutical Sciences* (19th ed., 1995) in detail.

The pharmaceutical composition of the present invention may be used for oral or parenteral administration. In case of parenteral administration, the composition may be administrated by intravenous infusion, subcutaneous infusion, intramuscular infusion, intraperitoneal infusion, percutaneous administration, etc. Specifically, the pharmaceutical composition of the present invention may be orally administrated.

The proper doses of the pharmaceutical composition of the present invention may be differently prescribed depending on various factors, such as preparation methods, administration methods, patient age, body weight, sex, morbidity, food, administration time, administration routes, excretion rate and response susceptibility. For example, the daily dose of the pharmaceutical composition of the present invention is 0.001 to 100 mg/kg.

The pharmaceutical composition of the present invention may be prepared as a single form through pharmaceutical preparation using pharmaceutically acceptable carriers and/or excipients, or as a form contained in a high capacity container according to methods, which may be easily performed by persons of ordinary skill in the art to which the present invention pertains. Dosage forms may be a form of oils or solutions of aqueous media, suspensions, syrups or emulsions, or a form of extracts, powders, powdered drugs, granules, tablets or capsules, and additionally include dispersants or stabilizers.

According to another aspect of the present invention, the present invention provides a food composition, wherein the pentadienoyl piperidine derivative or the pharmaceutically acceptable salt thereof of the present invention is contained as an active ingredient for improvement or relief of metabolic diseases selected from the group consisting of obesity, diabetes, dyslipidemia, fatty liver and insulin resistance syndrome.

Since the pentadienoyl piperidine derivative used in the present invention has been described above, the derivative is omitted to avoid excessive repetition.

When the composition of the present invention is prepared as a food composition, the components which generally are added in the process of food manufacturing are contained as active ingredients, as well as the piperidine derivative of the present invention. For example, the components include proteins, carbohydrates, fat, nutrients, seasoning agents and flavoring agents. The carbohydrates are general sugars, such as monosaccharides (for example, glucose, fructose, etc.), disaccharides (for example, maltose, sucrose, oligosaccharides, etc.), polysaccharides (for example, dextrin, cyclodextrin, etc.), and sugar alcohols, such as xylitol, sorbitol, erythritol, etc. As flavoring agents, natural flavoring agents (thaumatin, stevia extracts (for example, rebaudioside A, glycyrrhizin, etc.)) and synthetic flavoring agents (for example, saccharin, aspartame, etc.) may be used.

When, for example, the food composition of the present invention is prepared as a drink preparation, citric acid, high fructose corn syrup, sugar, glucose, acetic acid, malic acid, fruit juices, *Eucommia ulmoidies* extracts, jujube extracts, licorice extracts, and so forth may be contained besides piperonal which is an active ingredient in the present invention.

According to another aspect of the present invention, the present invention provides a method of preventing, improving, or treating metabolic diseases, wherein the method includes a step of administrating the composition including the pentadienoyl piperidine derivative or the pharmaceutically acceptable salt thereof of the present invention as an active ingredient to a subject in need and the metabolic diseases are selected from the group consisting of obesity, diabetes, dyslipidemia, fatty liver and insulin resistance syndrome are prevented, improved or treated.

As used herein, the term, "administration" or "administer" refers to that the therapeutic effective dose of the composition of the present invention is directly administrated into individuals (i.e., objects) who need the composition of the present invention to deliver the identical amount of the composition into the bodies of individuals. Accordingly, the term "administration" includes that the active ingredient (the pentadienoyl piperidine derivative or the pharmaceutically acceptable salt thereof) of the present invention is injected into the regions of lesions, and thus the term "administer" is used in the same way as "inject".

The term, "therapeutic effective dose" of the composition of the present invention refers to the content of extracts sufficient to provide a therapeutic or preventive effect to individuals who are administrated the composition, and thus also includes the meaning, "preventive effective dose". As used herein, the term, "individuals" include, without limit, humans, mice, rats, guinea pigs, dogs, cats, horses, cattle, pigs, monkeys, chimpanzees, baboons or rhesus monkeys. Specifically, an individual of the present invention is a human.

Since the pentadienoyl piperidine derivative used in the present invention has been described above, the derivative is omitted to avoid excessive repetition.

Advantageous Effects

Features and benefits of the present invention are summarized as follows:

(a) The present invention provides a novel pentadienoyl piperidine derivative and a pharmaceutical composition containing the derivative for prevention or treatment of metabolic diseases, and also provides a functional food composition using the derivative for improvement or relief of metabolic diseases and a method for prevention, improvement or treatment of metabolic diseases using the composition.

(b) The pentadienoyl piperidine derivative of the present invention inhibits the differentiation of preadipocytes, reduces body weight, visceral fat, blood lipid levels, and blood glucose levels, improves a blood liver function index, and suppresses metabolic inflammation responses. Thus, ultimately, the derivative can be usefully used as a medicine or a functional food composition, which exhibits the preventive or therapeutic activity for metabolic diseases selected from the group consisting of obesity, diabetes, dyslipidemia, fatty liver and insulin resistance syndrome.

DESCRIPTION OF DRAWINGS

FIG. 1B, LJ-2488; FIG. 1C, LJ-2495; FIG. 1D, LJ-2496). *, ** indicate Student's t-test. Substantial differences were observed compared to the DMSO-treated control group (*P<0.05 and **P<0.01).

FIG. 8A illustrates the concentrations of IL-6 and TNF-α, and FIG. 8B illustrates the concentrations of MCP-1 and leptin. Characters within the same row indicate significant differences, which were validated by one-way ANOVA and Duncan's multiple range test (P<0.05).

In FIG. 11A, an upper panel illustrates the representative gel images of RT-PCR analyses and a bottom panel illustrates the relative expression levels of the genes. The data was normalized relative to GAPDH mRNA, and all expression levels are values relative to ND mice. FIG. 11B illustrates the protein levels of p-CREB and total CREB, which were analyzed by Western blotting and normalized by β-actin protein. The data was obtained from three independent experiments (n=2 or 3 per an experiment). Characters above bars in the graphs indicate significant differences compared to other diet groups, which were validated by one-way ANOVA and Duncan's multiple range test (P<0.05).

In FIG. 12A, an upper panel illustrates the representative gel images of RT-PCR analyses and a bottom panel illustrates the relative expression levels of the genes. The data was normalized relative to GAPDH mRNA, and all expression levels are values relative to ND mice. FIG. 12B illustrates the protein levels of p-AMPK and total AMPK, which were analyzed by Western blotting and normalized by β-actin protein. The data was obtained from three independent experiments (n=2 or 3 per an experiment). Characters above bars in the graphs indicate significant differences compared to other diet groups, which were validated by one-way ANOVA and Duncan's multiple range test (P<0.05).

MODES OF THE INVENTION

Figure 1A:
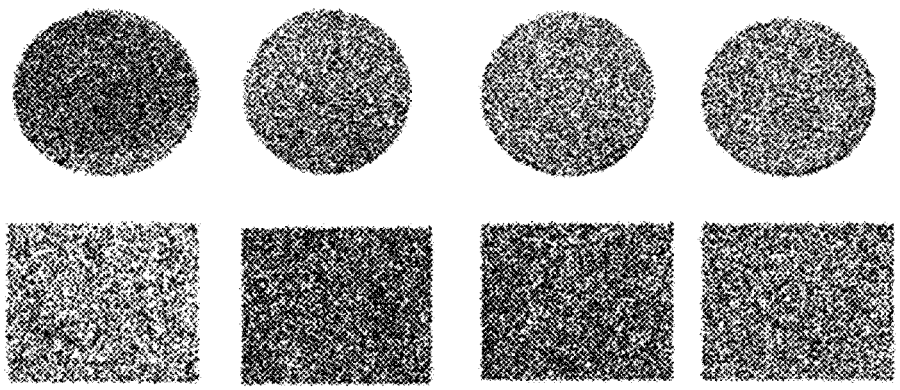
FIGS. 1A to 1D illustrate the inhibitory effects of the novel pentadienoyl piperidine compounds on adipocyte differentiation in 3T3L1 cells (FIG. 1A, LJ-2501.
Figure 1A:
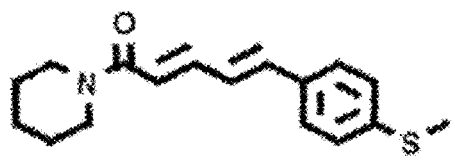
Figure 1A:
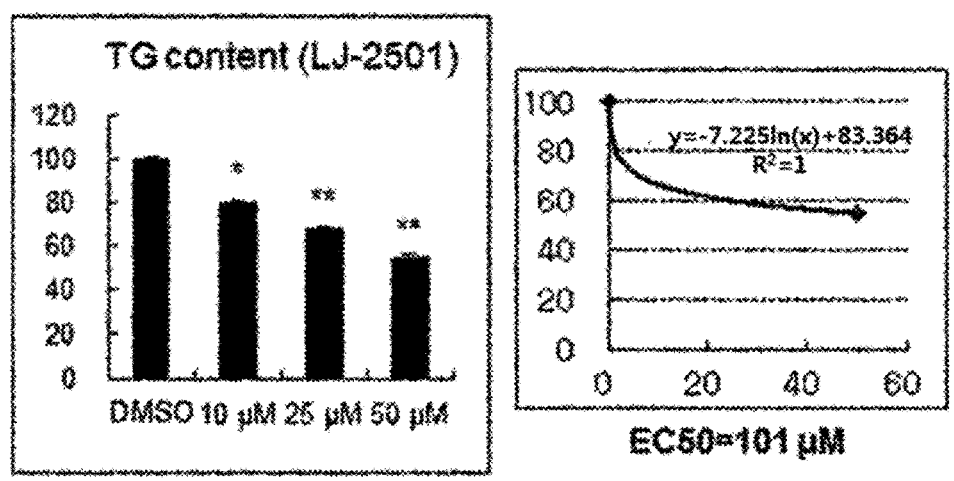
Figure 1B:
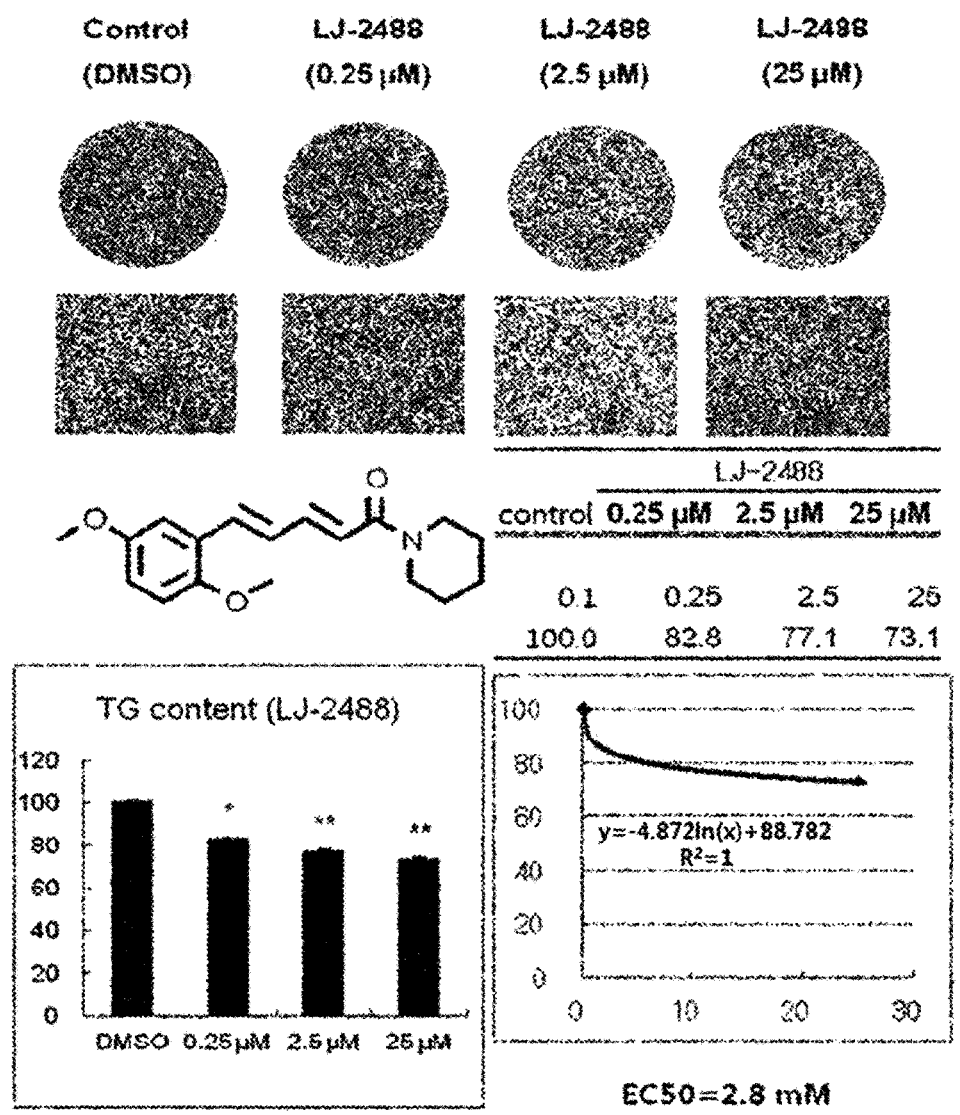
Figure 1C:
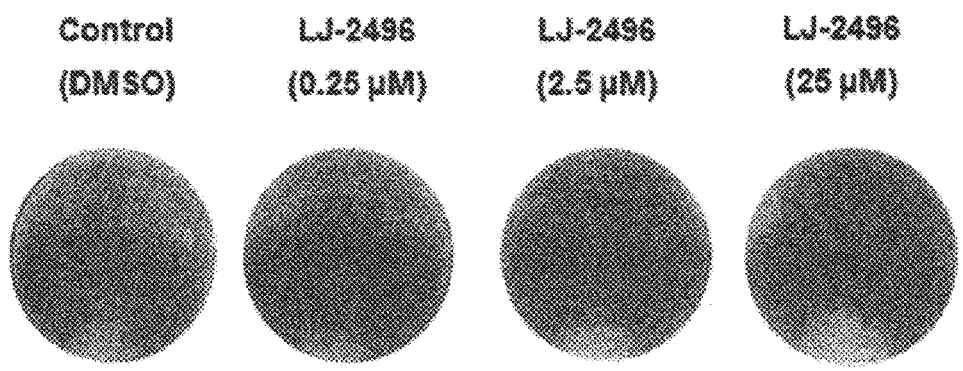
Figure 1D:
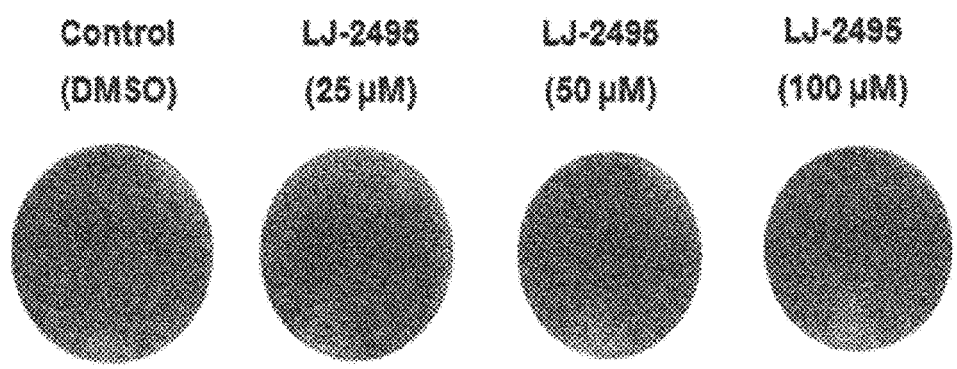

Hereinafter, the present invention will be described in more detail with reference to the following examples. It should be understand by those skilled in the art that the examples are for the purpose of specifically explaining the spirit of the invention and therefore, there is no intent to limit the invention to the examples.

EXAMPLES

Example 1: Synthesis of Compound 1) (2E,4E)-5-(4-(methylthio)phenyl)-1-(piperine-1-yl)penta-2,4-diene-1-one

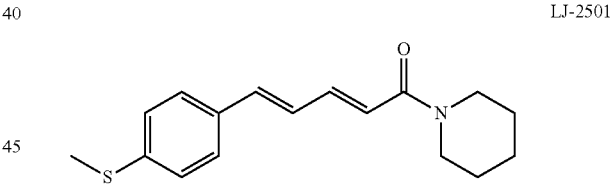

LJ-2501

(E)-diethyl 4-oxo-4-(piperine-1-yl)but-2-enyl phosphonate (50 mg, 0.17 mmol) and 4-methylthiobenzaldehyde (28 μL, 0.216 mmol) were dissolved in −10° C. THF (1.5 mL) and then potassium tert-buthoxide (0.51 mL, 0.51 mmol) was added thereto, followed by stirring for 20 minutes at the same temperature under an anhydrous reaction condition. The temperature of a resultant mixture was elevated to room temperature and then distilled water was added thereto, thereby terminating the reaction. EtOAc was added to a resultant product and then an oil layer was isolated therefrom. The isolated oil layer was washed with distilled water and a saturated NaCl solution and dried with anhydrous Na$_2$SO$_4$, followed by filtration. A resultant filtrate was subjected to vacuum distillation, thereby obtaining a residue. The residue was purified through column chromatography (hexane: EtOAc(2:1)). As a result, a target compound (17 mg, 28.3%) was obtained.

$^1$H NMR (500 MHz, CDCl$_3$): δ7.45-7.50 (dd, 1H, J=9.6, 14.6 Hz), 7.36 (bs, 1H), 7.34 (bs, 1H), 7.20 (bs, 1H), 7.18

(bs, 1H), 6.79-6.88 (m, 2H), 6.42-6.45 (d, 1H, J=14.6 Hz), 3.59 (t, 4H, J=5.9 Hz), 2.48 (s, 3H), 1.66 (m, 2H), 1.60 (m, 4H).

2) (2E,4E)-5-(2,5-dimethoxyphenyl)-1-(piperine-1-yl)penta-2,4-diene-1-one

LJ-2488

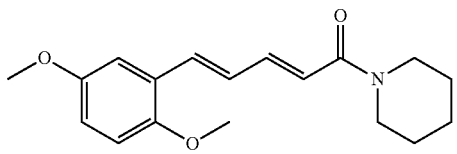

(E)-diethyl 4-oxo-4-(piperine-1-yl)but-2-enyl phosphonate (50 mg, 0.17 mmol) and 2,5-dimethoxybenzaldehyde (28.4 mg, 0.17 mmol) were dissolved in −10° C. THF (1.5 mL) and then potassium tert-buthoxide (0.51 mL, 0.51 mmol) was added thereto, followed by stirring for 20 minutes at the same temperature under an anhydrous reaction condition. The temperature of a resultant mixture was elevated to room temperature and then distilled water was added thereto, thereby terminating the reaction. EtOAc was added to a resultant product and then an oil layer was isolated therefrom. The isolated oil layer was washed with distilled water and a saturated NaCl solution and dried with anhydrous Na$_2$SO$_4$, followed by filtration. A resultant filtrate was subjected to vacuum distillation, thereby obtaining a residue. The residue was purified through column chromatography (hexane: EtOAc(2:1)). As a result, a target compound (40.7 mg, 78.6%) was obtained.
$^1$H NMR (500 MHz, CDCl$_3$) δ7.48-6.53 (dd, 1H, J=3.2 Hz), 7.16-7.19 (bs, 1H), 7.02 (bs, 1H), 6.88-6.95 (m, 1H), 6.81 (d, 1H, J=3.2 Hz), 6.42-6.48 (bs, 2H), 3.81 (s, 4H), 3.78 (s, 3H), 3.59 (t, 4H, J=3.2 Hz), 1.66 (m, 2H), 1.56-1.60 (m, 4H).

3) (2E,4E)-5-(4-ethoxyphenyl)-1-(piperine-1-yl)penta-2,4-diene-1-one

LJ-2495

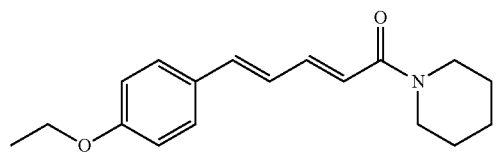

(E)-diethyl 4-oxo-4-(piperine-1-yl)but-2-enyl phosphonate (50 mg, 0.17 mmol) and 4-ethoxybenzaldehyde (30 μL, 0.216 mmol) were dissolved in −10° C. THF (1.5 mL) and then potassium tert-buthoxide (0.51 mL, 0.51 mmol) was added thereto, followed by stirring for 20 minutes at the same temperature under an anhydrous reaction condition. The temperature of a resultant mixture was elevated to room temperature and then distilled water was added thereto, thereby terminating the reaction. EtOAc was added to a resultant product and then an oil layer was isolated therefrom. The isolated oil layer was washed with distilled water and a saturated NaCl solution and dried with anhydrous Na$_2$SO$_4$, followed by filtration. A resultant filtrate was subjected to vacuum distillation, thereby obtaining a residue. The residue was purified through column chromatography (hexane: EtOAc (2:1)). As a result, a target compound (19 mg, 30.8%) was obtained.
$^1$H NMR (500 MHz, CDCl$_3$): δ7.44-7.49 (dd, 1H, J=4.6, 14.7 Hz), 7.36-7.38 (d, 2H, J=8.7 Hz), 6.84-6.86 (d, 2H, J=8.7 Hz), 6.78-6.80 (d, 2H, J=7.3 Hz), 6.39-6.42 (d, 1H, J=14.6 Hz), 4.03 (q, 2H, J=6.8 Hz), 3.58 (t, 4H, J=5.5 Hz), 1.65 (m, 2H), 1.60 (m, 4H), 1.41 (t, 3H, J=7.3 Hz).

4) (2E,4E)-1-(piperine-1-yl)-5-(4-propoxyphenyl)penta-2,4-diene-1-one

LJ-2496

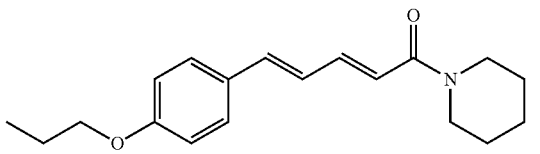

(E)-diethyl 4-oxo-4-(piperine-1-yl)but-2-enyl phosphonate (50 mg, 0.17 mmol) and 4-propoxybenzaldehyde (36 mg, 0.216 mmol) were dissolved in −10° C. THF (1.5 mL) and then potassium tert-buthoxide (0.51 mL, 0.51 mmol) was added thereto, followed by stirring for 20 minutes at the same temperature under an anhydrous reaction condition. The temperature of a resultant mixture was elevated to room temperature and then distilled water was added thereto, thereby terminating the reaction. EtOAc was added to a resultant product and then an oil layer was isolated therefrom. The isolated oil layer was washed with distilled water and a saturated NaCl solution and dried with anhydrous Na$_2$SO$_4$, followed by filtration. A resultant filtrate was subjected to vacuum distillation, thereby obtaining a residue. The residue was purified through column chromatography (hexane: EtOAc(2:1)). As a result, a target compound (21.1 mg, 32.6%) was obtained.
$^1$H NMR (500 MHz, CDCl$_3$): δ7.42-7.47 (dd, 1H, J=9.6, 14.7 Hz), 7.37 (d, 2H, J=8.2 Hz), 6.84-6.86 (d, 2H, J=8.2 Hz), 6.73-6.79 (m, 2H), 6.39-6.42 (d, 1H, J=14.6 Hz), 3.92 (t, 2H, J=6.8 Hz), 3.58 (bs, 4H), 1.76-1.83 (m, 2H), 1.65 (m, 2H), 1.59 (m, 4H), 1.02 (t, 3H, J=7.3 Hz).

Example 2: Adipocyte Differentiation Inhibition Effect Investigation of LJ-2501 using Mouse Preadipocyte Cell Line (3T3-L1)

1) Cell Culture and Oil-Red O Staining

Preadipocytes, 3T3L1 cells, were aliquoted into a 12-well plate and cultured in a DMEM medium containing 1% penicillin-streptomycin, 1% nonessential amino acid, and 10% fetal bovine serum (FBS) in a 5% CO$_2$ incubator at 37° C. until confluence. The 3T3L1 cells grown to confluence were cultured for two days in a medium containing 0.5 mM isobutyl-methylxanthine, 1 μM dexamethasone (MDI), and 1 μg/ml insulin, thereby being differentiated into adipocytes. Subsequently, the differentiated adipocytes were further cultured for two days in a DMEM medium including 1 μg/ml insulin, thereby being differentiated into mature adipocytes. Subsequently, the differentiated mature adipocytes were further cultured for 10 days while replacing a used DMEM medium with a new DMEM medium every two days. As a result, completely differentiated adipocytes were formed.

3T3-L1 cells were treated with each of a total of four novel compound types at different concentrations every two days from the first day of cell differentiation induction by addition of DMI. The structures and molecular weights of the four novel compounds are shown in Table 1. Each of the derivative compounds was dissolved in DMSO and then used. A negative control group including only DMSO was included in this experiment. Cell culture was carried out for 14 days. When differentiation was completed, a medium was removed and lipid droplets contained in differentiated adipocytes were stained. To stain the lipid droplets, cells were washed with phosphate buffered saline (PBS) twice and then fixed with 10% buffered neutral formalin for one hour, followed by washing with PBS once. Subsequently, 1 ml of Oil-red-O dye for staining lipid droplets red was fed into a 12-well plate and lipid droplets were stained for one hour, followed by washing with distilled water twice. To measure the concentration of neutral fat contained in the differentiated 3T3L1 cells, the stained lipid droplets were dissolved in 1 ml of isobutanol, followed by measuring an O.D value at 600 nm.

structure similar to LJ-2501 did not exhibit an adipocyte differentiation inhibition effect (FIGS. 1A to 1D).

Example 3: SIRT1 activation ability of LJ-2501

1) SIRT1 Activity Measurement Method

To analyze SIRT1 activity in a test tube, a deacetylation degree of acetylated lysine included in a substrate was measured using an SIRT1 Fluorometric Drug Discovery Kit (BML-AK555, ENZO Life Sciences Inc., NY, USA). 0.067 U/μl of a human recombinant SIRT1 enzyme and a test substance were mixed in a 96-well plate and reacted at 37° C. for 10 minutes. Subsequently, 167 μM substrate [$379^{th}$ to $382^{nd}$ amino acid peptide of human p53, Arg-His-Lys-Lys (Ac)] and 1667 μM $NAD^+$ were added thereto, followed by reacting at 37° C. for 30 minutes. To stop the reaction of SIRT1, 50 μL of a developer including 2 mM nicotinamide was added, followed by reacting at 37° C. for 30 minutes. Chromophoric fluorescence intensity was measured at 360 nm excitation and 460 nm emission.

TABLE 1

Structure of pentadienoyl piperidine compound

| No. | Derivative | IUPAC NOMENCLATURE | Structure | Molecular weight (g/mol) |
|---|---|---|---|---|
| 1 | LJ-2501 | (2E,4E)-5-(4-(methylthio)phenyl)-1-(piperine-1-yl)penta-2,4-diene-1-one | 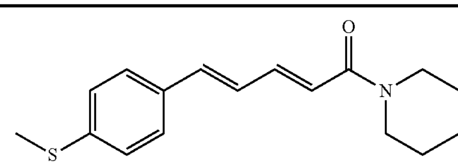 | 287.42 |
| 2 | LJ-2488 | (2E,4E)-5-(2,5-dimethoxyphenyl)-1-(piperine-1-yl)penta-2,4-diene-1-one | 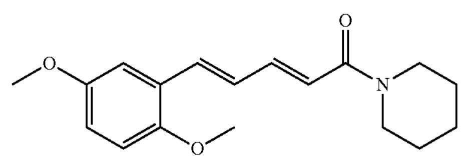 [SMILES: COc1ccc(OC)c(/C=C/C=C/C(=O)N2CCCCC2)c1] | 301.38 |
| 3 | LJ-2495 | (2E,4E)-5-(4-ethoxyphenyl)-1-(piperine-1-yl)penta-2,4-diene-1-one | 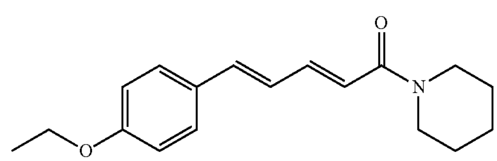 [SMILES: CCOc1ccc(/C=C/C=C/C(=O)N2CCCCC2)cc1] | 285.38 |
| 4 | LJ-2496 | (2E,4E)-1-(piperine-1-yl)-5-(4-propoxyphenyl)penta-2,4-diene-1-one | 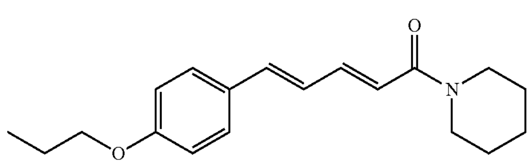 [SMILES: CCCOc1ccc(/C=C/C=C/C(=O)N2CCCCC2)cc1] | 299.41 |

2) Adipocyte Differentiation Inhibition Ability of LJ-2501 Compound

Figure 2A:
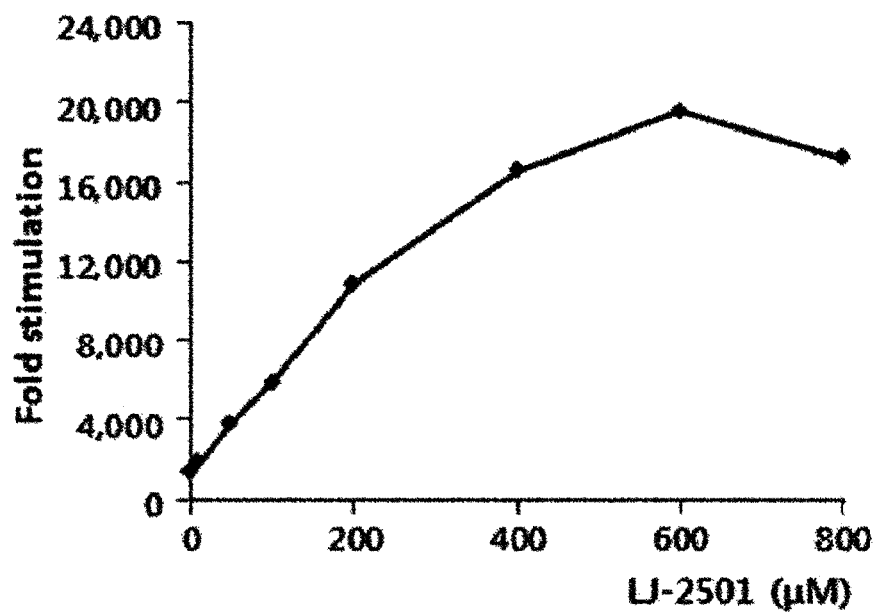
FIGS. 2A to 2C illustrate the capacity of LJ-2501 to activate SIRT1. SIRT1 activity (FIG. 2A) depending on the concentrations of LJ-2501, enzyme reaction kinetics (FIG. 2B) depending on the concentrations of a substrate (p53-382), and enzyme reaction kinetics (FIG. 2C) depending on the concentrations of a coenzyme ($NAD^+$) are illustrated, respectively.
Figure 2B:
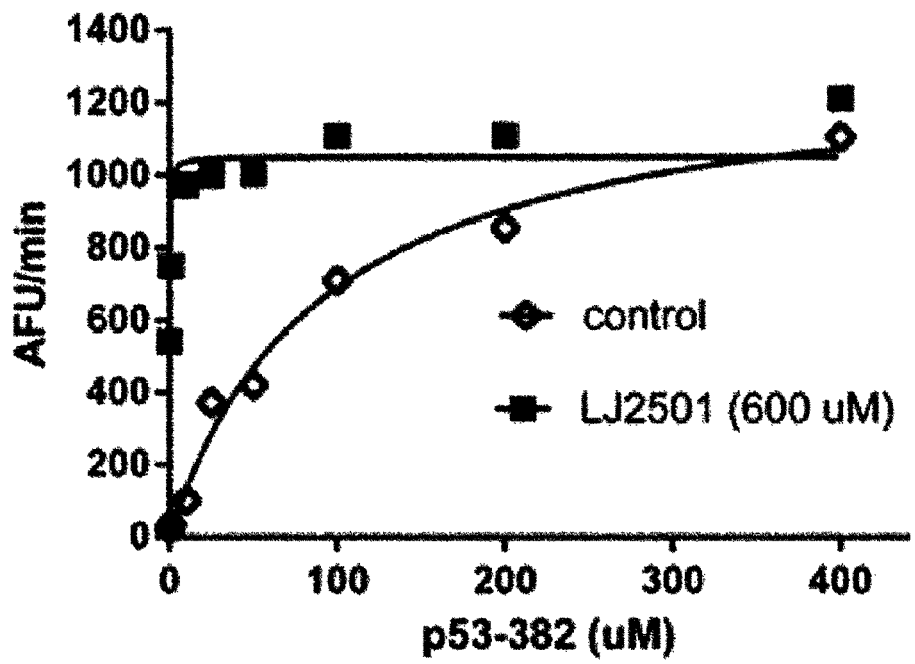
Figure 2C:
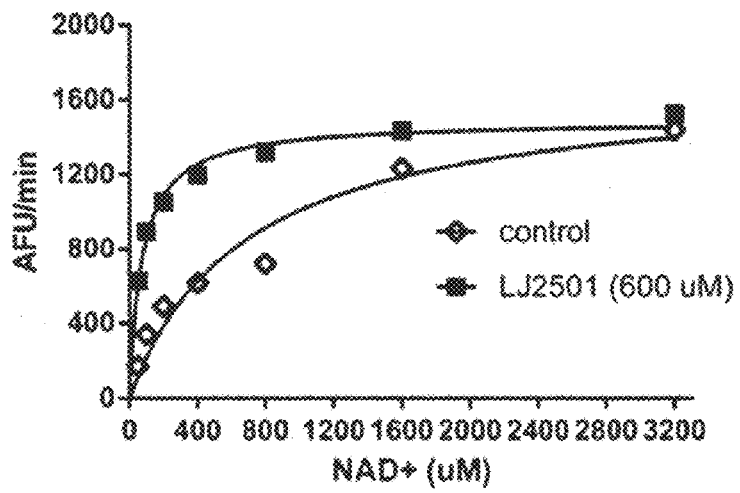

3T3L1 cells were treated with each of the four novel compound types at different concentrations and adipocyte differentiation inhibition effects thereof were measured. As results, it was confirmed that the adipocyte differentiation inhibition activity of LJ-2501 was most excellent ($EC_{50}$ value, 101 μM). LJ-2488 also exhibited a preadipocyte differentiation inhibition effect, but the effect thereof was much lower than that of LJ-2501 ($EC_{50}$ value, 2.8 mM). Meanwhile, LJ-2495 and LJ-2496 compounds having a 2) SIRT1 Activation Ability of LJ2501 Compound SIRT1 activity was measured while increasing the concentration of the LJ2501 compound. As a result, the SIRT1 activity was highest at a concentration of 600 μM (FIG. 2A). In the state in which LJ2501 (600 μM) was added, enzyme kinetics were measured while increasing the concentration of a substrate (p53-382) or ($NAD^+$). As a result, it was confirmed that LJ2501 functioned as an SIRT1 activator by reducing a Km value of a substrate (91 μM vs 0.13 μM) or a coenzyme (682 μM vs 74 μM) with respect to an enzyme (increasing affinity) without change in a Vmax value (FIGS. 2B and 2C).

Example 4: Weight and Visceral Fat Reduction Effects of LJ-2501 Compound in Mice 1) Experimental Diet Preparation and Experimental Animal Breeding An obesity induction diet used in this experiment was a high-fat diet (HFD: 40% fat calories, 17 g of lard+3% corn oil/100 g diet), and the compositions of diets including the LJ-2501, LJ-2488, LJ-2495, LJ-2496 compounds were identical to that of HFD, except that each of the compounds was included in an amount of about 0.05% (Table 2). As a control drug, an anti-obesity drug, sibutramine (Sibut), was added in an amount of about 0.01% to the high-fat diet and a normal diet group (Chow) was fed with commercial rodent chow.

TABLE 2

Experimental diet composition table (g/kg diet)

| Ingredients | High-fat diet (HFD) | LJ-2501 supplement diet (LJ2501) | LJ-2488 supplement diet (LJ2488) | Sibutramine supplement diet (Sibut) |
|---|---|---|---|---|
| Casein | 200 | 200 | 200 | 200 |
| DL-methionine | 3 | 3 | 3 | 3 |
| Corn starch | 111 | 110.5 | 110.5 | 110 |
| Sucrose | 370 | 370 | 370 | 370 |
| Cellulose | 50 | 50 | 50 | 50 |
| Corn oil | 30 | 30 | 30 | 30 |
| Lard | 170 | 170 | 170 | 170 |
| Vitamin complex | 12 | 12 | 12 | 12 |
| Mineral complex | 42 | 42 | 42 | 42 |
| Choline bitartrate | 2 | 2 | 2 | 2 |
| Cholesterol | 10 | 10 | 10 | 10 |
| Tert-butylhydroquinone | 0.04 | 0.04 | 0.04 | 0.04 |
| Experimental substance | — | 0.5 | 0.5 | 0.1 |
| Total (g) | 1,000 | 1,000 | 1,000 | 1,000 |
| Fat (% calories) | 39.0 | 39.0 | 39.0 | 39.0 |
| Total calories, kJ/kg diet | 19,315 | 19,315 | 19,315 | 19,315 |

5-week old 40 male C57BL/6J mice (Orient Bio., Korea) were fed with hard feed and accommodated in a laboratory environment for one week. Subsequently, in accordance with a randomized block method, the mice were randomly grouped into a normal diet group, a high-fat diet control group, two experimental substance groups, and two control drug groups and raised for a total of 10 weeks (n=8/group). Diets were supplied with water between 10 am and 11 am every day. An intake amount was measured every day and the body weights of the mice were measured every week. To prevent temporal weight change due to feed intake, feedboxes were removed and, after two hours, the body weights were measured. The experimental animals were fasted for 12 hours or more and then anesthetized with diethyl ether, followed by collecting blood, liver, and visceral adipose tissues (epididymal fat, perirenal fat, mesenteric fat, and retroperitoneal fat). The collected samples were washed with 0.1 M phosphate buffered saline (pH 7.4) and then weighed. Blood samples collected from abdominal aortas were centrifuged at 1000×g for 15 minutes, thereby separating plasma.

2) Change in Body Weight and Visceral Fat Weight

Figure 3A:
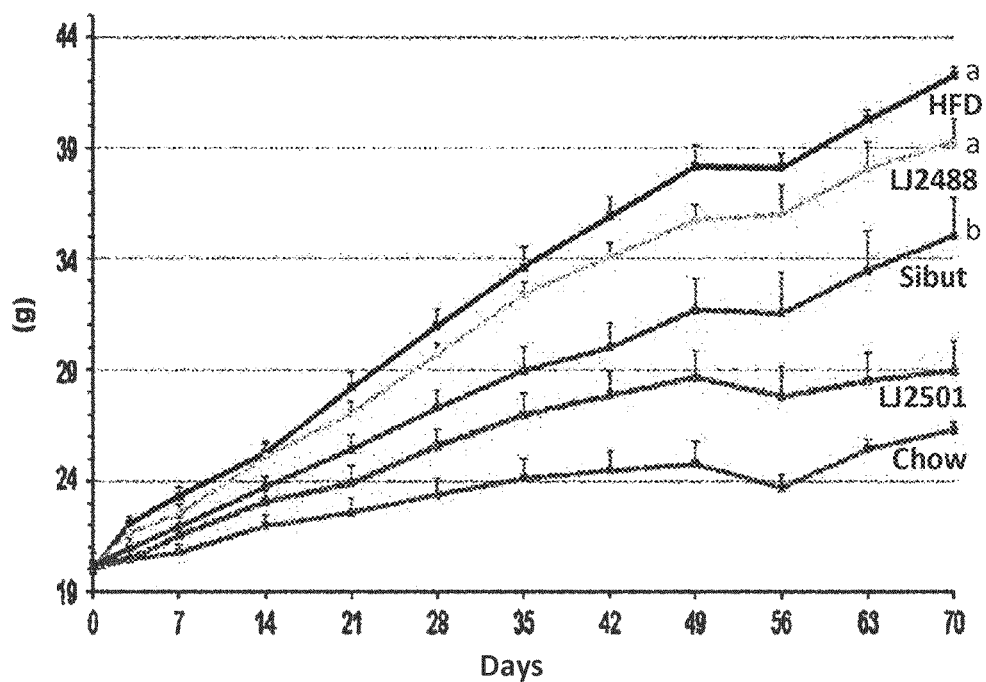
FIGS. 3A to 3C illustrate the body weight gains of mice fed research diets. The body weight changes of the respective mice (FIG. 3A) over time, and body weight gains (FIG. 3B) and the amounts of dietary intake (FIG. 3C) during a 10-week period of experimental breeding are illustrated, respectively. Each value is the average ±S.E. (n=8). Characters above bars in the graphs indicate significant differences, which were validated by one-way ANOVA and Duncan's multiple range test (P<0.001).
Figure 3B:
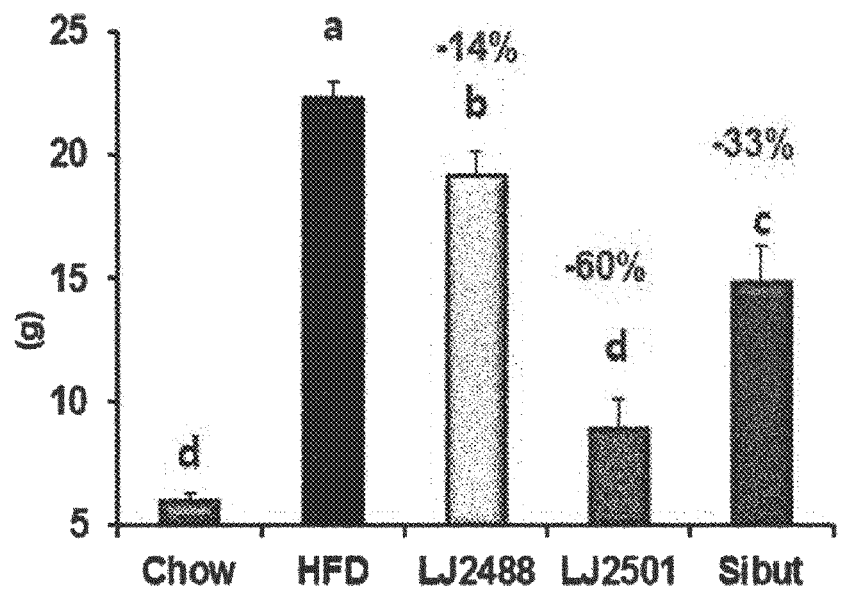
Figure 3C:
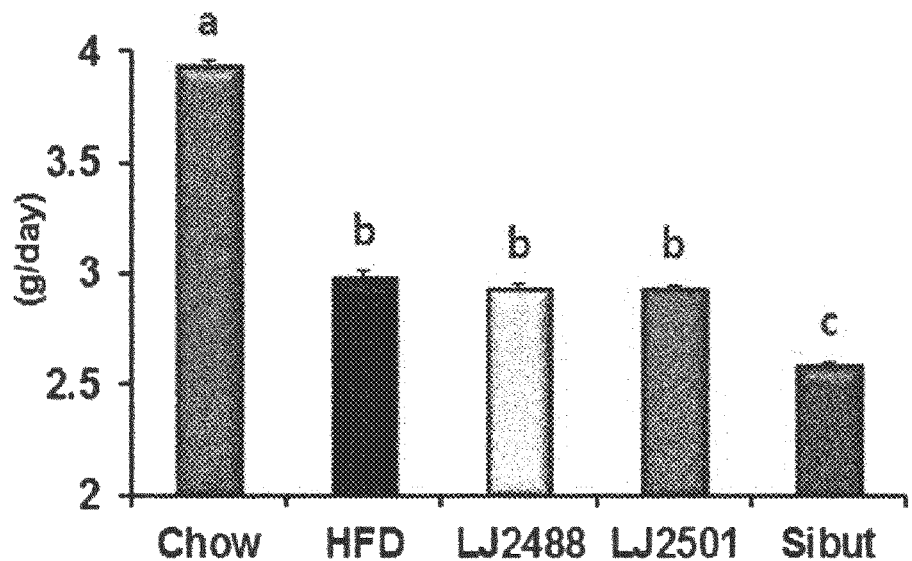

The mice were fed with experimental diets for 10 weeks and then final body weights and increased body weights thereof were investigated. With regard to the increased body weights, a cumulative weight gain in a group supplemented with LJ-2501 significantly reduced by 60%, compared to a high-fat diet control group (HFD). It was confirmed that the weight reduction effect by LJ-2501 was excellent compared to that by LJ-2488 (−14%) and superior compared to that by a control drug, sibutramine (−33%). A diet intake amount of mice fed with LJ-2501 was not greatly different from that of the HFD control group. Accordingly, it can be confirmed that the anti-obesity effect of LJ-2501 was not caused by loss of appetite (FIGS. 3A to 3C).

Figure 4A:
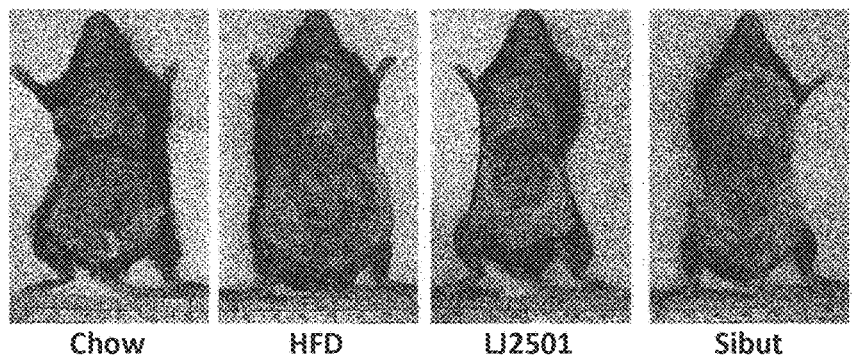
FIGS. 4A and 4B illustrate the images of abdominal sections and the visceral fat weights of different parts of mice fed research diets. Each value is the average ±S.E. (n=8). Characters above bars in the graphs indicate significant differences, which were validated by one-way ANOVA and Duncan's multiple range test (P<0.001).
Figure 4B:
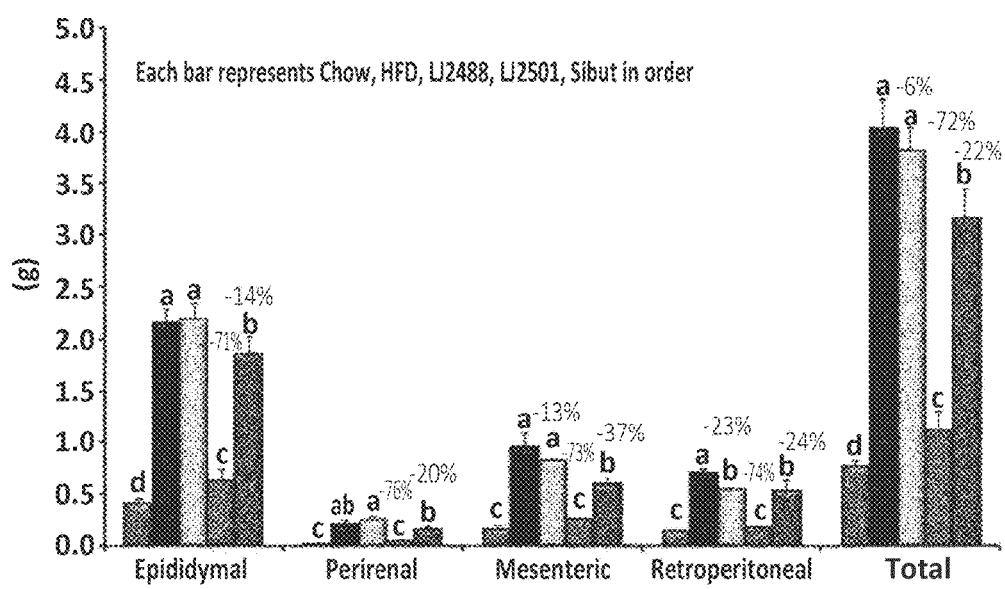

It can be observed with the naked eye that, from an abdominal section image of a mouse fed with the experimental diet for 10 weeks (FIG. 4A), a visceral fat amount in the LJ-2501 group remarkably reduced, compared to that in the HFD group. Epididymal fat, perirenal fat, mesenteric fat, and retroperitoneal fat constituting visceral fats were respectively removed and the weights thereof were measured. As results, the group fed with LJ-2501 exhibited a significant reduction in the epididymal fat, the perirenal fat, the mesenteric fat, and the retroperitoneal fat, compared to the control group (HFD). A total weight of visceral fats including the four fat types was significantly reduced by 72% (FIG. 4B). It was confirmed that the visceral fat reduction effect of LJ-2501 was excellent compared to that of LJ-2488 (−6%) and superior compared to that of a control drug, sibutramine (−22%). Accordingly, it was confirmed that LJ2501 compound had excellent body weight reduction and visceral fat amount reduction effects.

Example 5: Hyperlipidemia Prevention and Treatment Effects of LJ-2501 Compound 1) Biochemical Blood Analysis Method Using the aforementioned experimental animals raised for 10 weeks, the concentrations of a total of cholesterol, neutral fat, and glucose in plasma and lipid components in liver tissue were measured as follows. The concentrations of a total of cholesterol, neutral fat, and free fatty acid in plasma were respectively measured twice using a commercial measurement kit (Bio Clinical System).

2) Change in Plasma Lipid Concentration

Figure 5A:
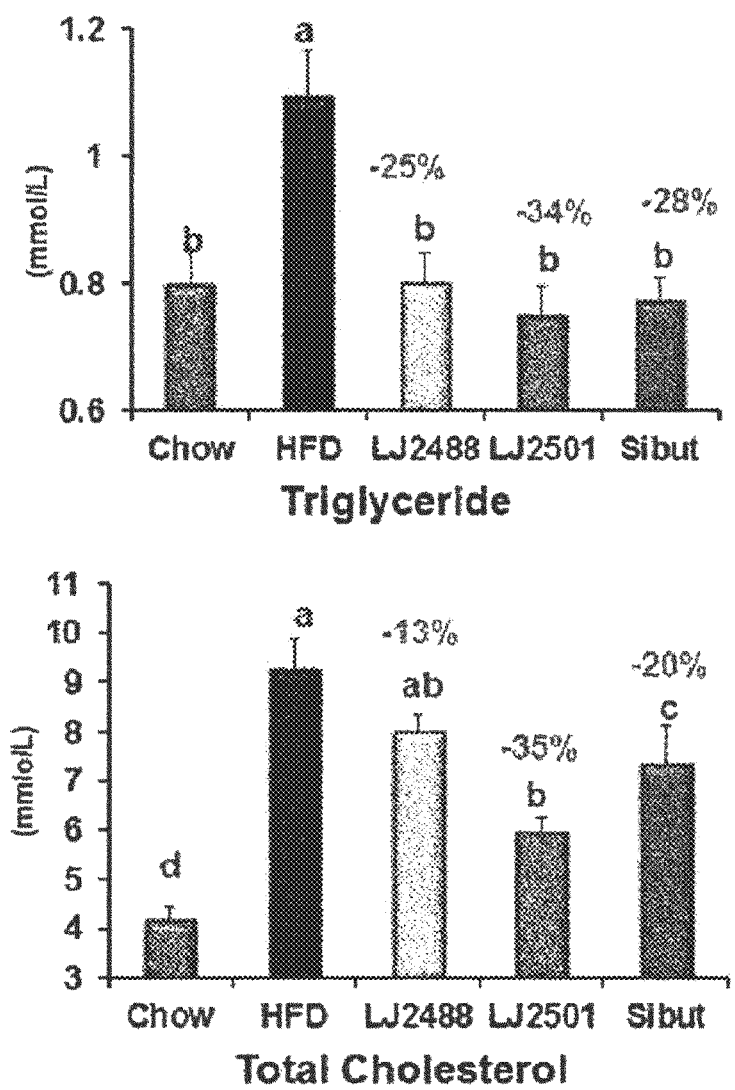
FIGS. 5A to 5C illustrate the blood lipid levels of mice fed research diets. Characters within the same row indicate significant differences, which were validated by one-way ANOVA and Duncan's multiple range test (P<0.05).
Figure 5B:
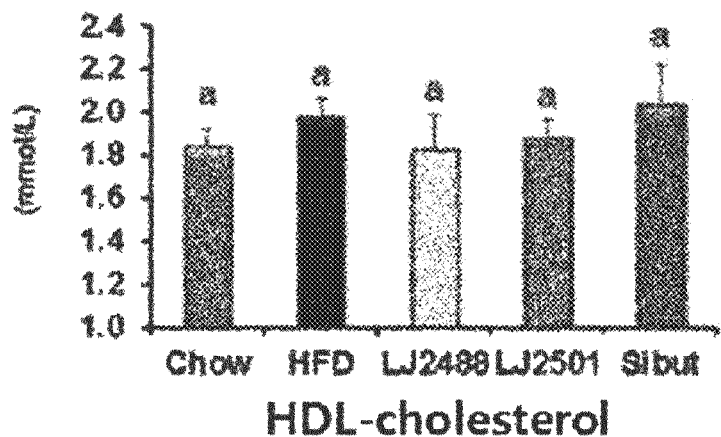
Figure 5B:
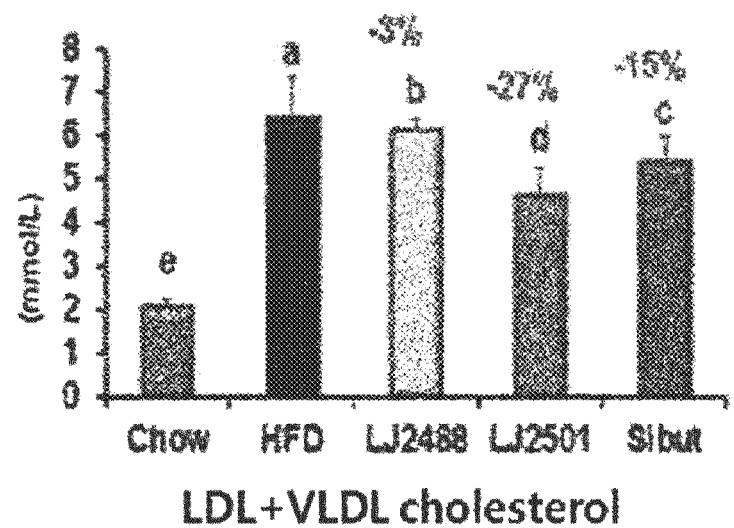
Figure 5C:
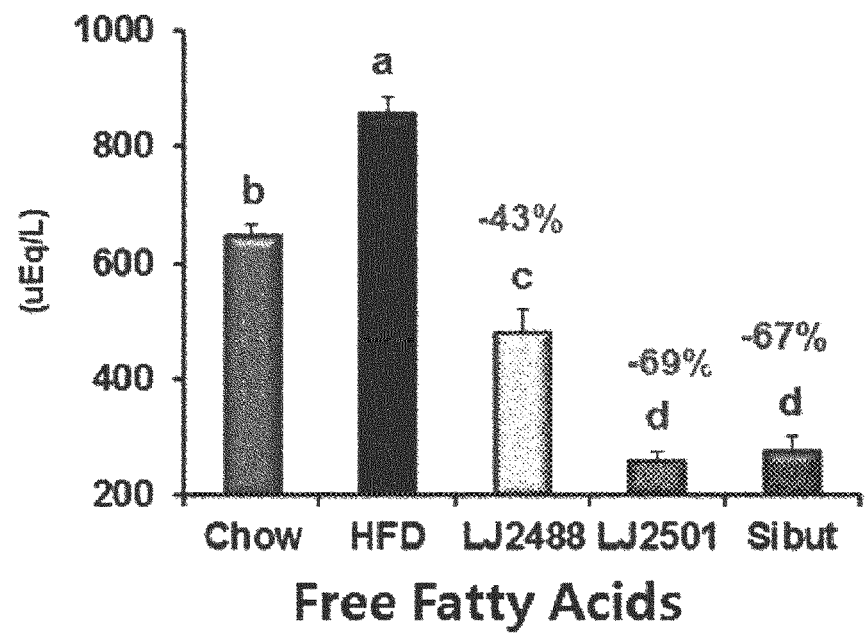

Examining plasma lipid concentrations in the mice fed with the experimental diets for 10 weeks, the group fed with LJ2501 exhibited a significant reduction of 34% in a neutral fat concentration, a significant reduction of 35% in a total cholesterol concentration (FIG. 5A), a significant reduction of 27% in an LDL+VLDL cholesterol concentration (FIG. 5B), and a significant reduction of 69% in a free fatty acid concentration (FIG. 5C), compared to the high-fat diet control group (HFD). Meanwhile, blood HDL cholesterol concentrations in the HFD group and all experimental groups were not significantly different (FIG. 5B). It was confirmed that neutral fat, cholesterol, and free fatty acid concentration reduction effects of LJ-2501 were excellent compared to those of LJ-2488 and superior than those of a control drug, sibutramine. Accordingly, it can be confirmed that the LJ2501 compound has excellent effect of improving hyperlipidemia induced by a high-fat diet.

Example 6: Non-Alcoholic Fatty Liver Prevention and Treatment Effects of LJ-2498 Compound 1) Method of Analyzing Lipid Concentration of Liver Tissue Lipid components were extracted from liver tissue in accordance with the method by Folch, et al. (Folch J, Lees M, Sloane Stanley G H. A simple method for the isolation and purification of total lipids from animal tissues. *J Biol*

*Chem.* 1957; 226:497-509). In particular, 1 mL of distilled water was added to 0.25 g of a liver tissue sample and then homogenized by means of a Polytron homogenizer (IKA-WERKE GmbH & Co., Ultra-Turrax, Staufen, Germany). To the homogenized solution, 5 mL of a solution including chloroform and methanol (mixed in a ratio of 2:1, v/v) was added, followed by uniformly mixing. Subsequently, centrifugation was carried out at 1000×g for 10 minutes and a lower solution was separated. To a formed supernatant, 2 mL of a mixture including chloroform and methanol (mixed in a ratio of 2:1, v/v) was added, followed by repeating the same procedure. As a result, lipid components were completely isolated from the liver samples. To an obtained lower solution, 3 mL of a mixture including chloroform, methanol, and 0.05% $CaCl_2$ (mixed in a ratio of 3:48:47, v/v/v) was added, followed by mixing for one minute. Subsequently, centrifugation was carried out at 1000×g for 10 minutes. A final lower solution was collected and completely dried with a nitrogen gas. Subsequently, the dried lipid was dissolved in 1 mL of methanol and used for lipid component analysis. The concentrations of neutral fat and cholesterol in the lipid extracts extracted from the liver tissue were measured using the same commercial lipid analysis kit (Bio Clinical System) as that used in the plasma analysis.

2) Analysis Method of Hepatic Function Indicators in Blood

Glutamate oxaloacetate transferase (GOT) and glutamate pyruvate transferase (GPT) activity in serum during fasting were measured by means of an automatic biochemical analyzer (Express Plus, Chiron Diagnostics Co., USA). A kit for analysis was purchased from Bayer (Tarrytown, N.Y., USA).

3) Changes in Liver Weights and Lipid Concentrations in Liver Tissues

Figure 6A:
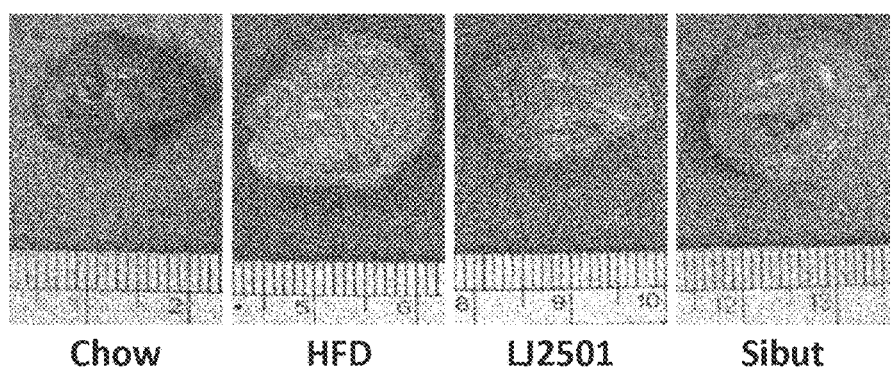
FIGS. 6A and 6B illustrate images of liver tissue (FIG. 6A) and liver weights (FIG. 6B) of mice. Each value is the average ±S.E. (n=8). Characters within the same row indicate significant differences, which were validated by one-way ANOVA and Duncan's multiple range test (P<0.05).
Figure 6B:
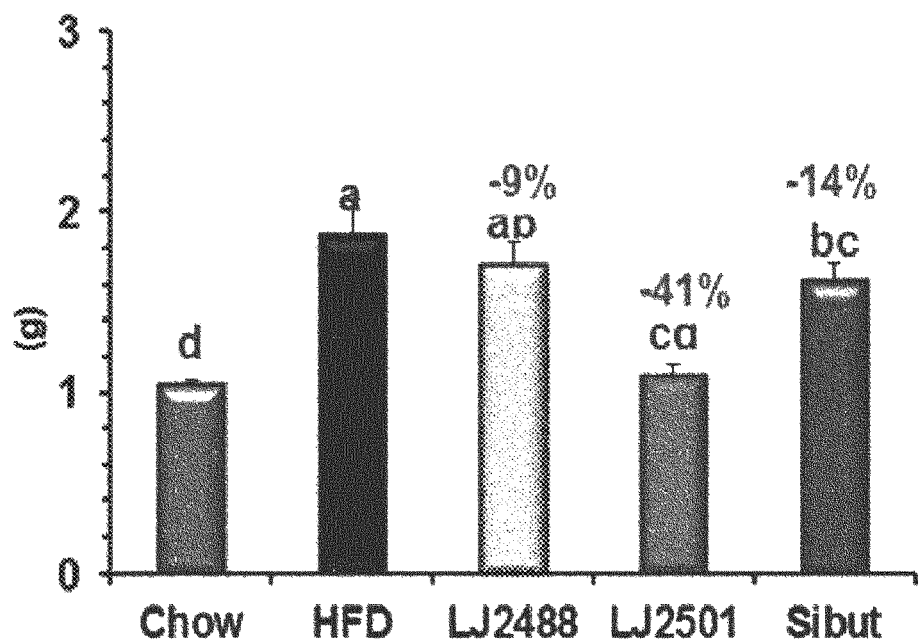

Photographs of liver tissue extracted from the mice fed with the experimental diets for 10 weeks are illustrated in FIG. 6A. It was observed that, in the case of the high-fat diet control group (HFD), the size of the liver tissue was large and the color thereof was light, compared to the Chow group. Meanwhile, the size of the liver extracted from the mouse fed with the LJ2501 compound was relatively small and the color thereof was dark, compared to that from the HFD group. Accordingly, it can be assumed that the fatty liver symptom of the mouse fed with the LJ2501 compound was alleviated. The liver tissue extracted from the experimental animals was weighted. As a result, it was confirmed that a liver weight of the group fed with LJ2501 significantly reduced by 41%, compared to the high-fat diet control group (FIG. 6B).

Figure 7A:
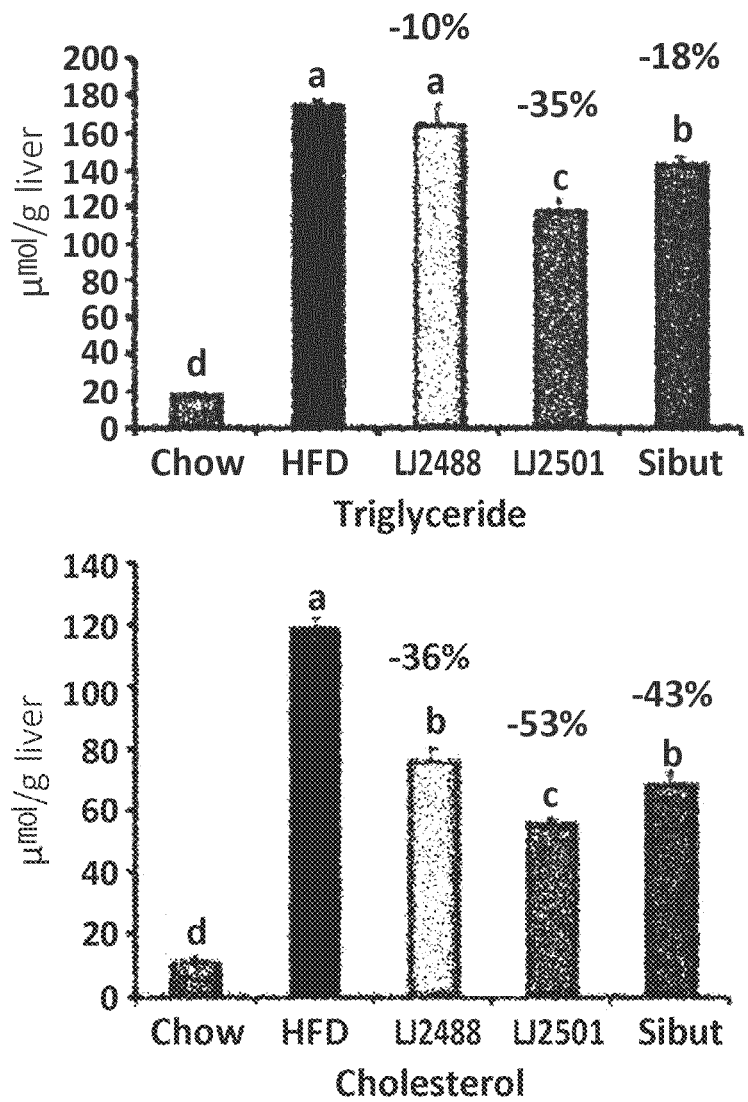
FIGS. 7A and 7B illustrate the lipid concentrations in liver tissue [neutral fat, cholesterol (FIG. 7A), free fatty acids (FIG. 7B)] and liver function indices (FIG. 7B) of mice. Characters within the same row indicate significant differences, which were validated by one-way ANOVA and Duncan's multiple range test (P<0.05).
Figure 7B:
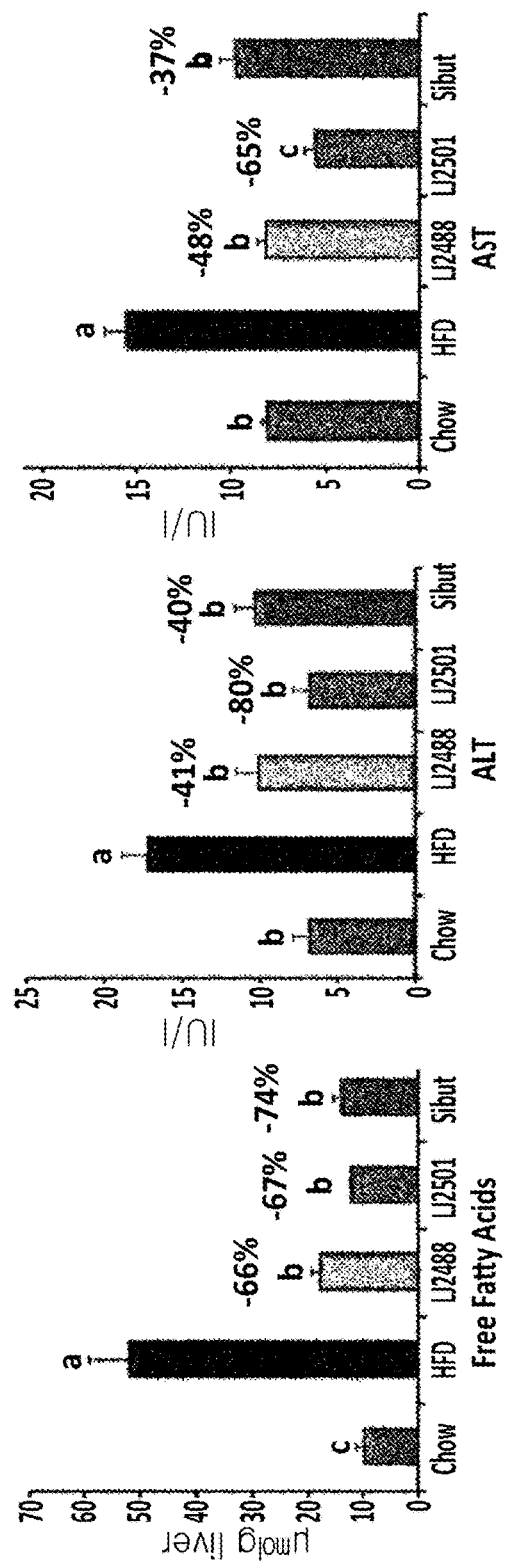

Examining lipid concentrations in liver tissues, the group fed with LJ2501 exhibited a significant reduction of 35% in a neutral fat concentration, a significant reduction of 53% in a cholesterol concentration, a significant reduction of 77% in a free fatty acid concentration, and significant reductions of 60-65% in hepatic function indexes (alanine aminotransferase, ALT; aspartate aminotransferase, AST) in the blood, compared to the high-fat diet control group (HFD) (FIGS. 7A and 7B). It was confirmed that such liver tissue neutral fat cholesterol and free fatty acid concentration reduction effects of LJ-2501 were excellent compared to those of LJ-2488 and superior compared to those of a control drug, sibutramine. Accordingly, it can be confirmed that the LJ2501 compound remarkably relieves fatty liver observed in obesity induced by a high-fat diet.

Example 7: Metabolic Inflammatory Reaction Inhibition Effect of LJ-2501 Compound 1) Method of Analyzing Concentrations of Inflammatory Cytokines in Blood The concentrations of TNFα, MCP-1, IL-6, leptin, and insulin in plasma were measured according to an ELISA method using the Mouse Adipokine Magnetic Bead Panel kit (MADKMAG-71K, EMD Millipore Corporation, Mass., USA).

2) Change in Inflammatory Cytokine Concentration in Blood

With regard to an inflammatory reaction occurring due to excessive supply of nutrients or metabolites, a new term, "metaflammation," recently appeared. In addition, obesity is indicated as "chronic and low-level inflammation" and research into a correlation between obesity and the immune system is actively underway. As an example, toll-like receptor 4 (TLR4) involved in an innate immune response plays important roles in inflammatory reaction and insulin resistance pathways using dietary fat (particularly, saturated fatty acid) as a ligand. When obesity is induced by a high-fat diet, the level of free fatty acids (particularly, saturated fatty acids) in body fluids increases. In addition, when free fatty acids, as a ligand, are bound to TLR4, IKK is activated, whereby NF-kB is activated and secretion of inflammatory cytokines, such as TNF-α and IL-6, is facilitated. As a result, an inflammatory reaction occurs. In addition, it is known that TNF-α and IL-6 phosphorylate a serine residue of an insulin receptor substrate (IRS) by activating cytokine signaling 3 (SOCS3) and JNK, thereby inhibiting sugar transport and inducing insulin resistance of the liver or peripheral tissues, such as muscle tissue.

Figure 8A:
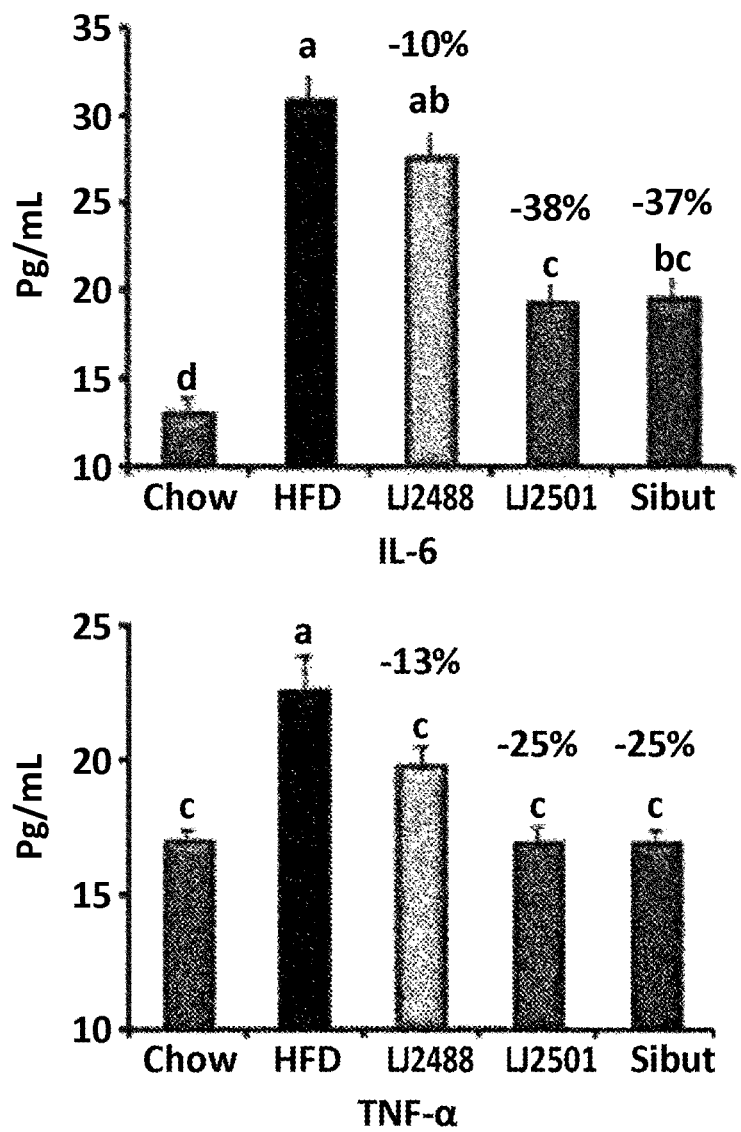
FIGS. 8A and 8B illustrates the cytokine concentrations in the blood of mice.
Figure 8B:
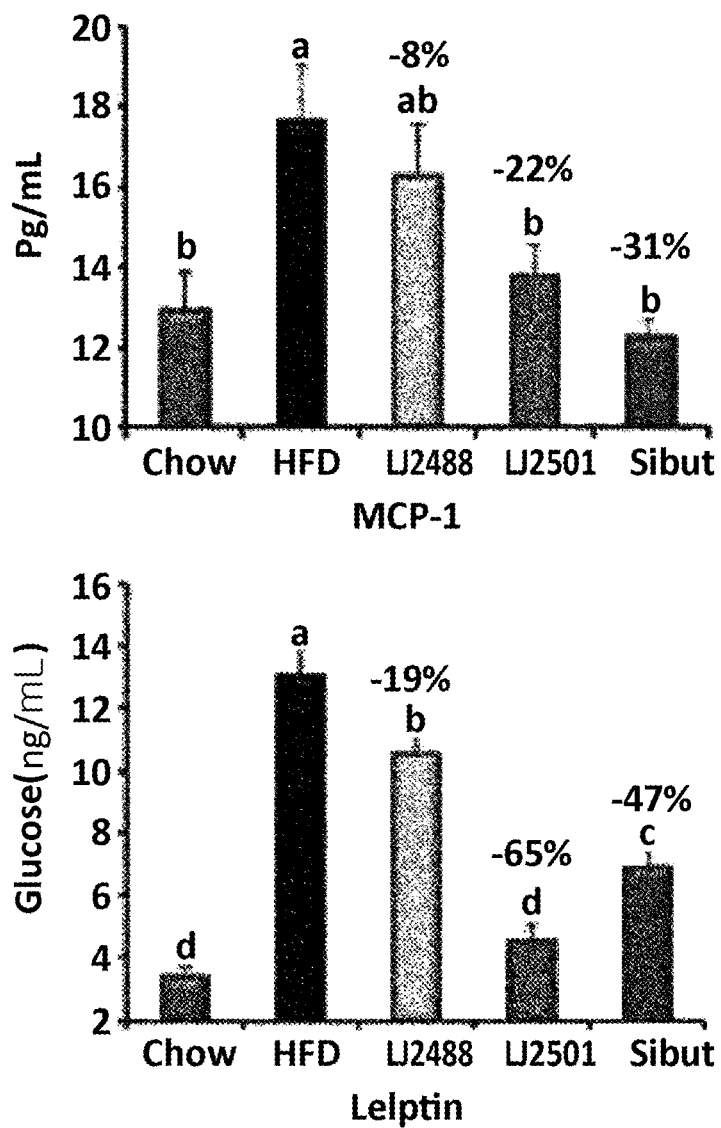
Figure 9A:
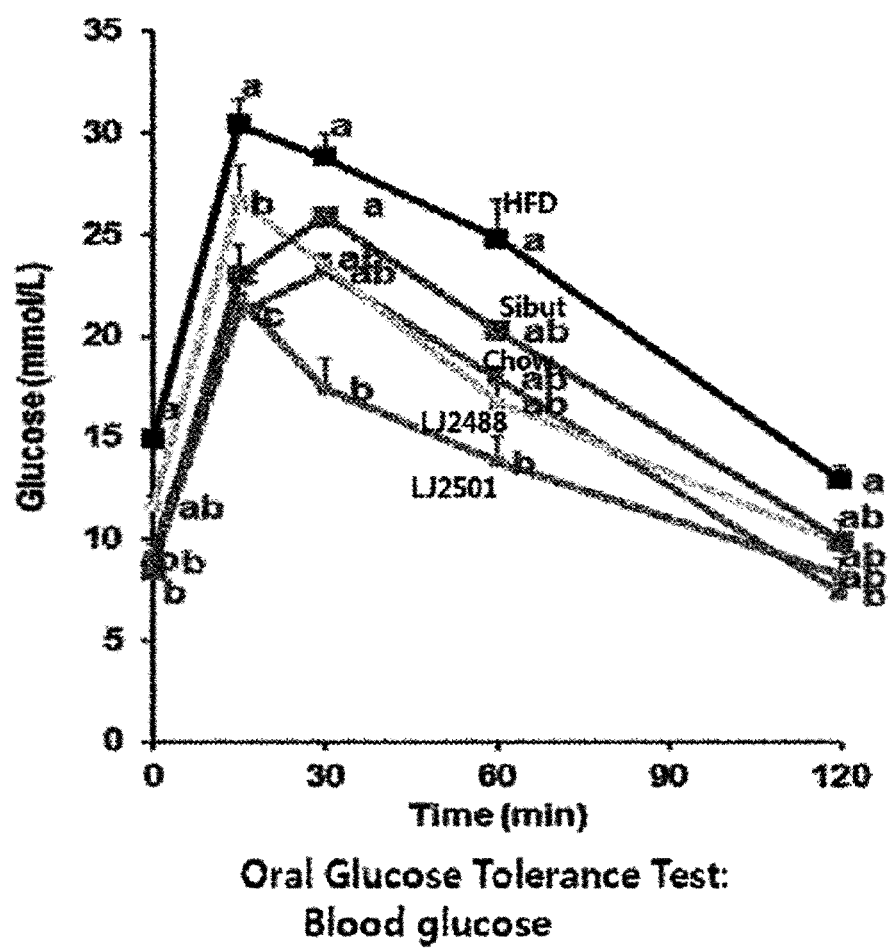
FIGS. 9A to 9E are the results of oral glucose tolerance tests for mice fed research diets. The results for oral glucose tolerance (FIG. 9A) and its AUC (FIG. 9B), fasting blood glucose (FIG. 9C), fasting blood insulin (FIG. 9D) and insulin resistance indices (HOMA-IR, FIG. 9E) are illustrated, respectively. Characters within the same row indicate significant differences, which were validated by one-way ANOVA and Duncan's multiple range test (P<0.05).
Figure 9B:
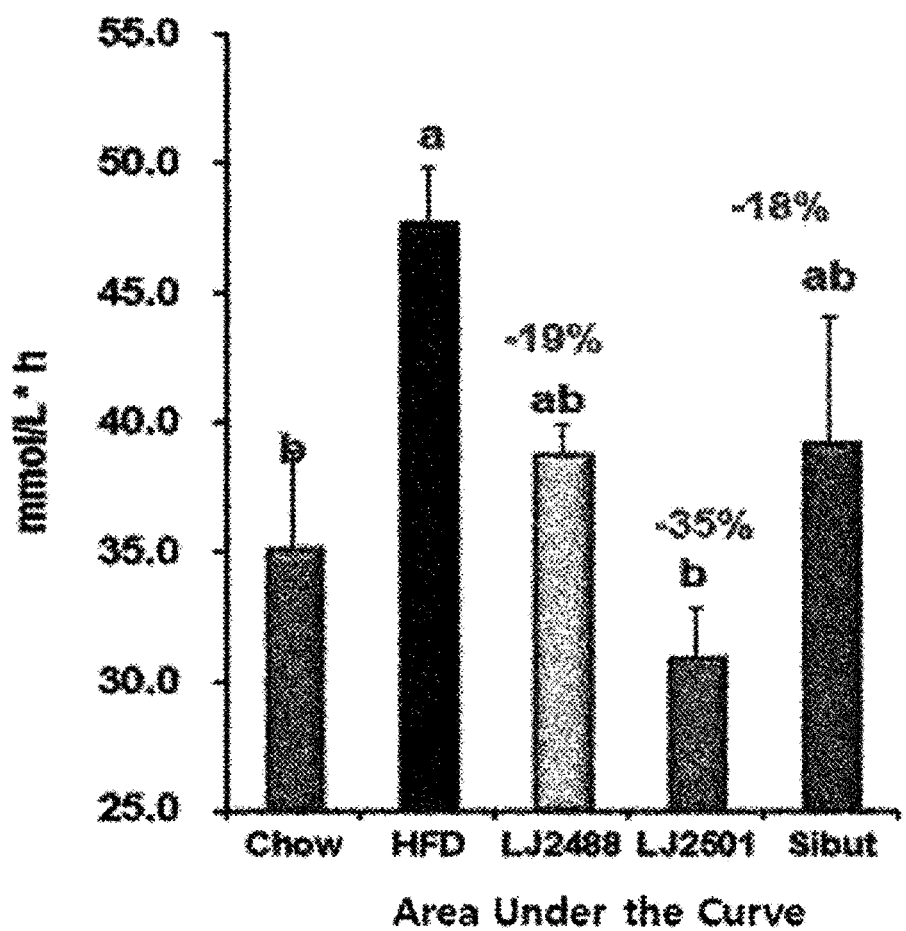
Figure 9C:
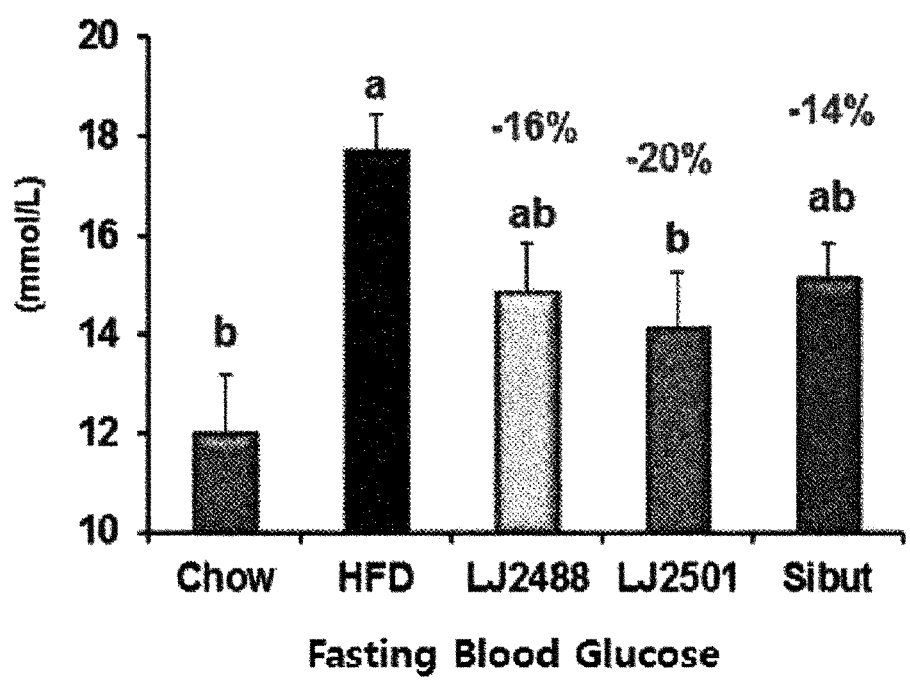
Figure 9D:
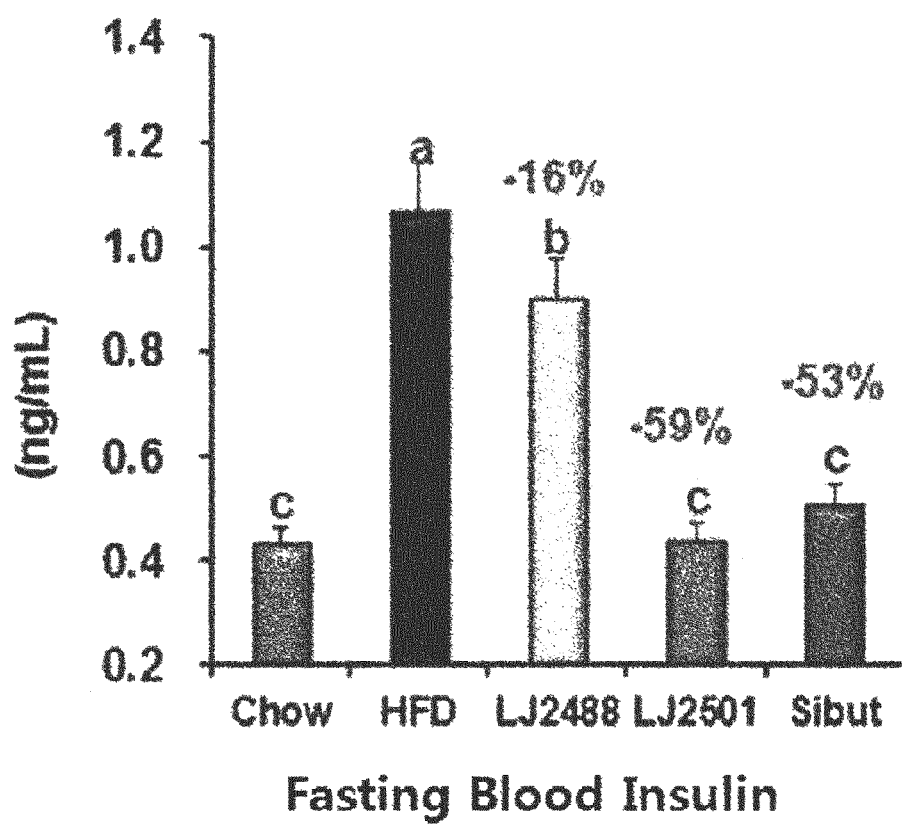
Figure 9E:
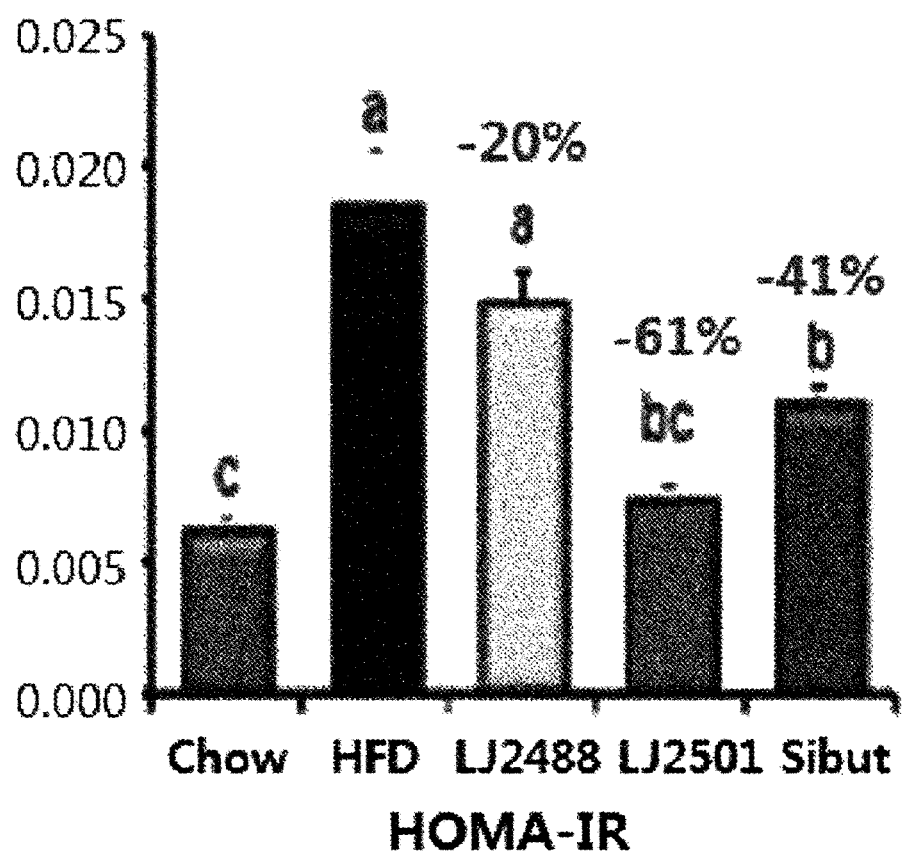

Examining inflammatory cytokine concentration in the blood, it was confirmed that the LJ2501 intake group exhibited a significant reduction of 38% in IL-6, a significant reduction of 25% in TNF-α (FIG. 8A), a significant reduction of 22% in MCP-1, and a significant reduction of 25% in leptin, compared to the high-fat diet control group (HFD) (FIG. 8B). It was confirmed that the inflammatory cytokine concentration reduction effect of LJ-2501 was excellent compared to that of LJ-2488.

Example 8: Type 2 Diabetes Prevention and Treatment Effects of LJ-2501 Compound

1) Method of Testing Resistance to Orally Administered Glucose

The experimental animals were fasted for 18 hours after being raised eight weeks for experiment and orally administered d-glucose in an amount of 2 g/kg body weight. At 15 minutes, 30 minutes, 60 minutes, 120 minutes after the d-glucose administration, blood was collected from the tail veins of the mice. A glucose concentration in the collected blood was measured by means of a strip-operated blood glucose sensor (ONETOUCH Ultra, Inverness Medical Ltd. Stockport, UK).

2) Method of Measuring Blood Glucose and Insulin Concentrations during Fasting

A glucose concentration in plasma during fasting was measured by means of an automatic biochemical analyzer (Express Plus, Chiron Diagnostics Co., USA) and a kit reagent for analysis was purchased from Bayer (Tarrytown, N.Y., USA). An insulin concentration in plasma was measured using the Rat Insulin RIA kit (LINCO Research, Inc, St. Charles, USA).

3) Result of Resistance Test to Orally Administered Glucose 2 g glucose/10 ml distilled water/kg BW were orally administered to the mice and then blood was collected from the tail veins thereof at time intervals of 15 minutes, 30 minutes, 60 minutes, and 120 minutes. A glucose concentration of the collected blood was measured. As results, in the case of the group fed with the LJ2501 compound, blood glucose concentrations were reduced in all time slots, compared to the HFD group. In addition, an area under the curve (AUC) value with respect to a blood glucose concentration was calculated and, as a result, the group fed with LJ2501 compound showed a significant reduction of 35%, compared to the HFD group. Meanwhile, mice fed with a high-fat diet were supplemented with the LJ2501 compound for 10 weeks and then a blood glucose concentration during fasting was measured. As a result, these mice exhibited a significant reduction of 20%, compared to the HFD group. In addition, a blood insulin concentration thereof was significantly reduced by 59%. An insulin resistance index (HOMA-IR), which was calculated based on these two values, also exhibited a significant reduction of 61% (FIGS. 9A to 9E). Accordingly, it can be confirmed that the LJ2501 compound has an excellent effect in improving resistance to orally administered glucose and blood glucose increases induced by a fat diet during fasting. In addition, it can be confirmed that insulin resistance and Type 2 diabetes improvement effects of the LJ2501 compound are excellent compared to those of LJ2488 and a control drug, sibutramine.

Example 9: Investigation on the Regulatory Mechanism for Anti-Obesity and Metabolic Disease of LJ-2501 Compound 1) RNA Isolation and Confirmation According to Trizol Method 1 ml of a TRIzol solution per 0.1 g of epididymal fat tissue was added to the pulverized tissue, followed by centrifuging at 4° C. and 12,000×g for 10 minutes. A supernatant was transferred into a new tube and then 200 μl of chloroform was added thereto, followed by vortexing. This process was repeated twice and then a supernatant was transferred into a new tube. Subsequently, isopropanol and the supernatant were mixed in a ratio of 1:1 and strongly shook ten times, followed by standing at room temperature for 10 minutes. Subsequently, centrifugation was carried out at 12,000×g and 4° C. for 10 minutes, followed by removing a supernatant and adding 1 ml of 70% ethanol to the remaining precipitate. Subsequently, centrifugation was carried out at 7,500×g and 4° C. for five minutes. Ethanol was removed and then the tube containing an RNA precipitate was dried at room temperature for five minutes. The dried RNA pellet was dissolved in nuclease free water. The concentrations of the extracted RNA samples were measured at wavelengths of 260 nm and 280 nm by means of a UV/VIS spectrophotometer (Beckman Coulter, DU730). In addition, the extracted RNA samples were electrophoresed on an agarose gel to confirm the quality of the RNA samples.

2) Reverse Transcription-Polymerase Chain Reaction (RT-PCR) Method

The RNA samples extracted from epididymal fat tissue were subjected to reverse transcription using oligo dT primers and the Superscript reverse transcription enzyme (GIBCO BRL, Gaithersburg, Md., USA), thereby synthesizing cDNAs. Each of the synthesized cDNAs was used as a template and 5' and 3' flanking sequences of cDNA of each of genes to be amplified were used as primers, thereby performing PCR. Sequences of the used primers are summarized in Table 3. 1 μl of each of amplified PCR products was electrophoresed on a 1% agarose gel and a DNA band was observed.

TABLE 3

| Primer-specific gene | Primer | Sequence (5' 3') | Annealing temperature (° C.) | PCR product (bp) |
|---|---|---|---|---|
| Peroxisome proliferator activated receptor gamma 2 (PPARγ2) | F<br>R | TTCGGAATCAGCTCTGTGGA<br>CCATTGGGTCAGCTCTTGTG | 55 | 148 |
| CCAAT/enhancer binding protein alpha (C/EBPα) | F<br>R | TCGGTGCGTCTAAGATGAGG<br>TCAAGGCACATTTTTGCTCC | 55 | 187 |
| CD36 antigen (CD36) | F<br>R | ATGACGTGGCAAAGAACAGC<br>GAAGGCTCAAAGATGGCTCC | 55 | 160 |
| Fatty acid synthase (FAS) | F<br>R | TTGCCCGAGTCAGAGAACC<br>CGTCCACAATAGCTTCATAGC | 55 | 171 |
| Lipoprotein lipase (leptin) | F<br>R | CTCCAAGGTTGTCCAGGGTT<br>AAAACTCCCCACAGAATGGG | 55 | 143 |
| Cytochrome C oxidase subunit 2 (COX2) | F<br>R | CCGAGTCGTTCTGCCAATAG<br>AACCCTGGTCGGTTTGATGT | 55 | 159 |
| Mitochondrial transcription factor A (TFAM) | F<br>R | AGTGTGGCAGTCCATAGGCA<br>CAGTGCTTTTAGCACGCTCC | 55 | 123 |

TABLE 3-continued

| Primer-specific gene | | Primer Sequence (5' 3') | Annealing temperature (° C.) | PCR product (bp) |
|---|---|---|---|---|
| Nuclear respiratory factor-1 (NRF-1) | F<br>R | TTTCATGGACCCAGGCATTA<br>TGGTGGCCTGAGTTTGTGTT | 55 | 119 |
| Sirtuin 1 (SIRT1) | F<br>R | AGCTCCTTGGAGACTGCGAT<br>ATGAAGAGGTGTTGGTGGCA | 55 | 182 |
| Peroxisome proliferative activated receptor γ coactivator 1α (PGC-1α) | F<br>R | TAAATCTGCGGGATGATGGA<br>GTTTCGTTCGACCTGCGTAA | 55 | 117 |
| Uncoupling protein 1 (UCP1) | F<br>R | GGTTTTGCACCACACTCCTG<br>ACATGGACATCGCACAGCTT | 55 | 111 |
| SREBP1c (SREBP1c) | F<br>R | TTGTGGAGCTCAAAGACCTG<br>TGCAAGAAGCGGATGTAGTC | 55 | 94 |
| Liver X receptor (LXR) | F<br>R | TCCTACACGAGGATCAAGCG<br>AGTCGCAATGCAAAGACCTG | 55 | 119 |
| Lipoprotein lipase (LPL) | F<br>R | TGCCGCTGTTTTGTTTTACC<br>TCACAGTTTCTGCTCCCAGC | 55 | 172 |
| Acetyl-Co-A carboxylase (ACC) | F<br>R | TGATGTCAATCTCCCCGCAGC<br>TTGCTTCTTCTCTGTTTTCTCCC | 60 | 353 |
| Glyceraldehyde-3-phosphate dehydrogenase (GAPDH) | F<br>R | AGAACATCATCCCTGCATCC<br>TCCACCACCCTGTTGCTGTA | 55 | 321 |

3) Western Blotting

A predetermined amount of visceral fat or liver tissue was homogenized with liquid nitrogen and a lysis buffer in a mortar and then centrifuged at 13,000 rpm and 4° C. for 20 minutes. Subsequently, a middle layer was collected and subjected to protein quantification according to the Bradford method. 50 μg of a protein was electrophoresed on an SDS polyacryamide gel and then electro-blotted on hyperfilm PVDF. A reaction was carried out using a corresponding antibody and detection was performed using ECL.

4) Investigation on the Regulatory Mechanism for Lipogenesis

Figure 10:
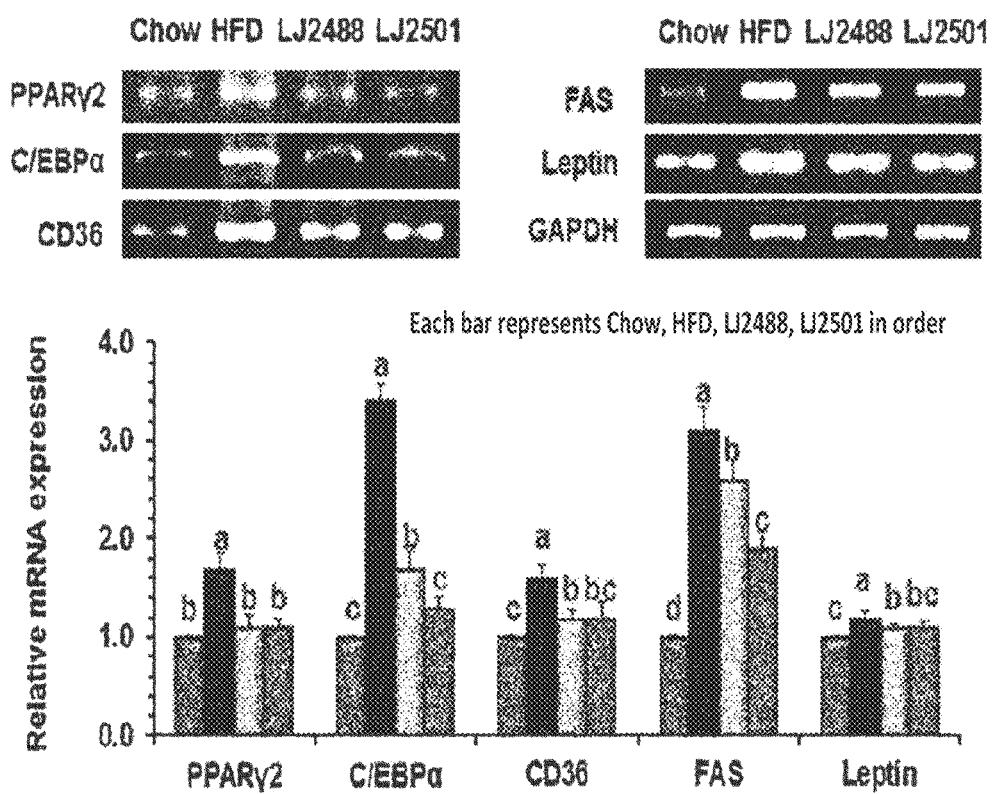
FIG. 10 illustrates the expression changes of genes related to adipose tissue generation in mouse visceral fat tissues. An upper panel illustrates the representative images of RT-PCR analyses and a bottom panel illustrates the relative expression levels of the genes. The data was normalized relative to GAPDH mRNA, and all expression levels are values relative to mice fed Chow diets. Each piece of data was obtained from three independent experiments (n=2 or 3 per experiment). Characters above bars in the graphs indicate significant differences compared to other diet groups, which were validated by one-way ANOVA and Duncan's multiple range test (P<0.05).

Adipogenesis is defined as a process, whereby a preadipocyte proliferates and differentiates into a mature adipocyte, and during the process, changes in cellular morphologies and gene expression patterns are involved. As a result of adipogenesis, lipids are accumulated, and adipose tissue-specific genes, such as AP2 (fatty acid binding protein), LPL (lipoprotein lipase), and FAS (fatty acid synthase), are expressed. The expression of the genes is mainly regulated by three transcription factors, including PPARγ (peroxisome proliferator activated receptor gamma), C/EBPs (CCAAT enhancer-binding proteins) and SREBP-1c (sterol regulatory binding protein-1c). When expression levels of mRNAs in the epididymal fat tissue were determined using RT-PCR, C/EBPα and PPARγ2, which act as important transcription factors in the generation of adipose tissues, and target genes thereof, such as CD36, FAS (fatty acid synthase) and leptin, were significantly increased in the HFD group compared to the ND group. Whereas the increased mRNAs, including C/EBPα and PPARγ2, and target genes thereof, in the HFD group were reduced in the LJ2501 group, exhibiting similar expression levels with the Chow group. Accordingly, the results suggested that LJ2501 supplements have an effect of reducing the amount of visceral fat by inhibiting gene expression of the transcription factors and the target genes thereof which have critical roles in the generation of the adipose tissues in the visceral adipose tissue (FIG. 10).

5) Investigation on the Regulatory Mechanism for Thermogenesis

Mitochondrial dysfunction relates to aging, heart diseases, gastrointestinal disorders, endocrine disorders and neurological disorders, and mitochondrial fatty acid oxidation disorders have been known to cause fatty liver through increasing glucose production in the liver tissue and inducing hypertriglyceridemia. An electron transport system in mitochondria generates a proton concentration gradient between inner and outer mitochondrial membranes, which acts as a driving force to produce ATP through F0F1-ATPase. However, in case F0F1-ATPase does not work properly, the driving force generated by a proton concentration gradient is released through UCPs (uncoupling proteins), whereby heat is produced. Recently, it has been reported that UCPs facilitate thermogenesis in the adipose tissue while balancing the oxidation-reduction through the energy-consuming reaction, and thus USPs have received attraction as a new target for obesity treatment.

Figure 11A:
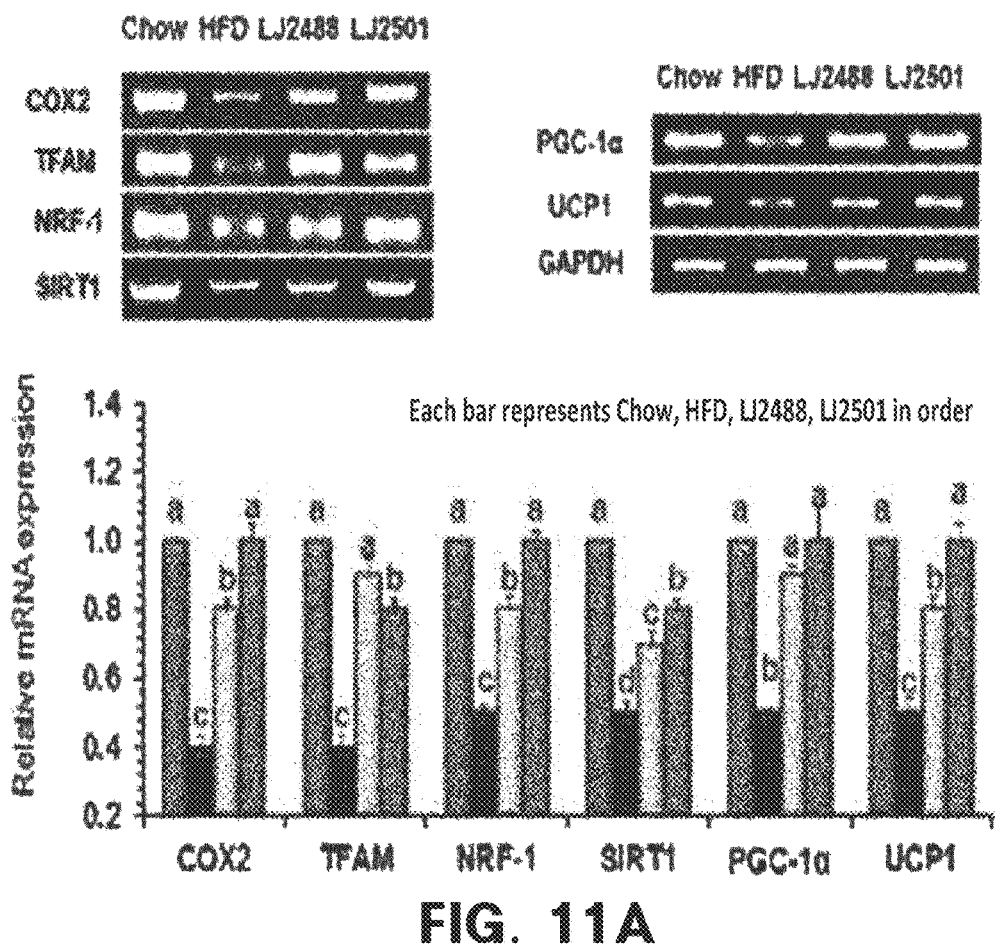
FIGS. 11A and 11B illustrate the expression changes of genes related to thermogenesis in visceral fat tissue in mice.
Figure 11B:
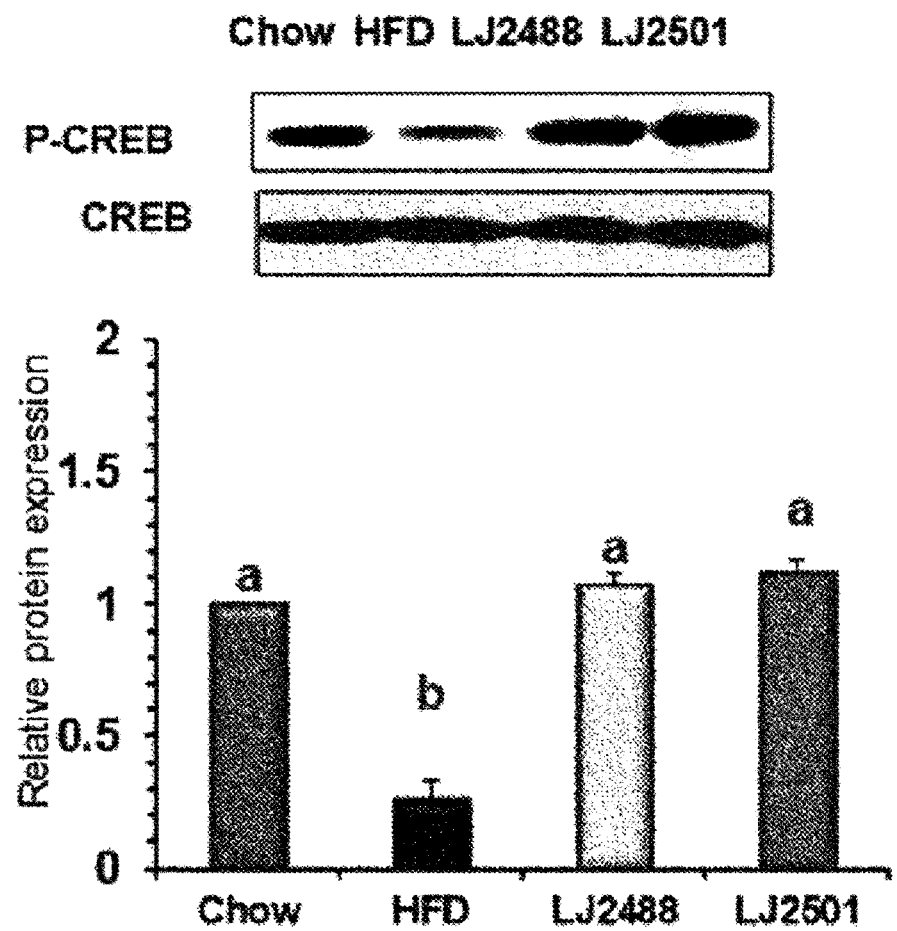

In mice fed high-fat diets, PKA (protein kinase A) activity was reduced in the visceral adipose tissue, by which the phosphorylation of CREB was decreased. As a result, the expression of PGC-1α (peroxisome proliferator-activated receptor γ coactivator-1 alpha) was reduced due to the decreased level of CREB phosphorylation. Additionally, the expression of sirtuin 1 (SIRT1), an enzyme catalyzing the deacetylation of PGC-1α, was decreased, by which UCP1 expression was reduced. Whereas, in mice fed LJ250 diets, the gene expression levels of PGC-1α, SIRT1, and UCP1, which had been decreased by high-fat diets, were increased in the visceral adipose tissue, exhibiting similar expression levels with the Chow group, and also the phosphorylation level of CREB proteins was increased in the LJ250 group. Additionally, LJ2501 diets exhibited an anti-obesity effect, remarkably improving thermogenesis in the visceral adipose tissue, which was inhibited by obesity (FIGS. 11A and 11B).

Besides mitochondrial respiration, mitochondrial biogenesis has an important role in improving thermogenesis capability. PGC-1α activates NRF-1 (nuclear respiratory factor-1), and then activated NRF-1 affects mitochondrial biogenesis through activating the promoter of COX2 (cytochrome C oxidase subunit 2) in the electron transport system. TFAM (mitochondrial transcription factor A), another target of NRF-1, has a role in replication and transcription of mitochondria DNA. In the present study, LJ2501 diets have been confirmed to increase mitochondrial biogenesis through increasing the expression levels of NRF-1, COX2, and TFAM, which play important roles in mitochondrial biogenesis (FIG. 11A).

6) Investigation on the Regulatory Mechanism for Lipogenesis

Figure 12A:
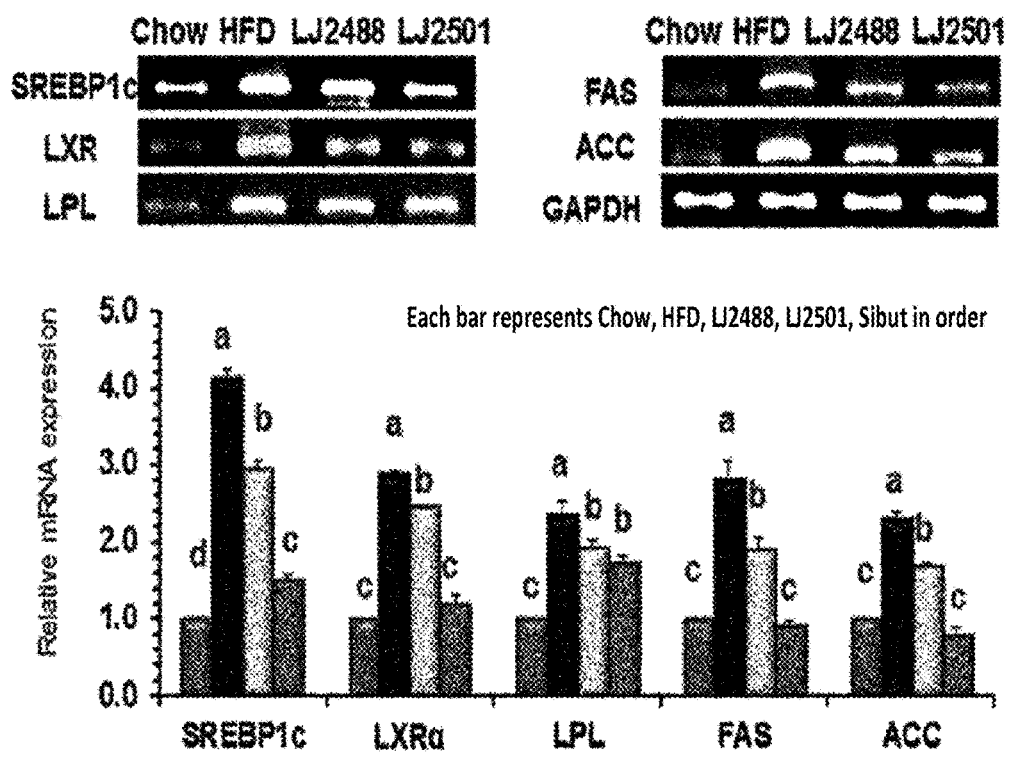
FIGS. 12A and 12B illustrate the expression changes of genes related to lipogenesis in mice liver tissue.
Figure 12B:
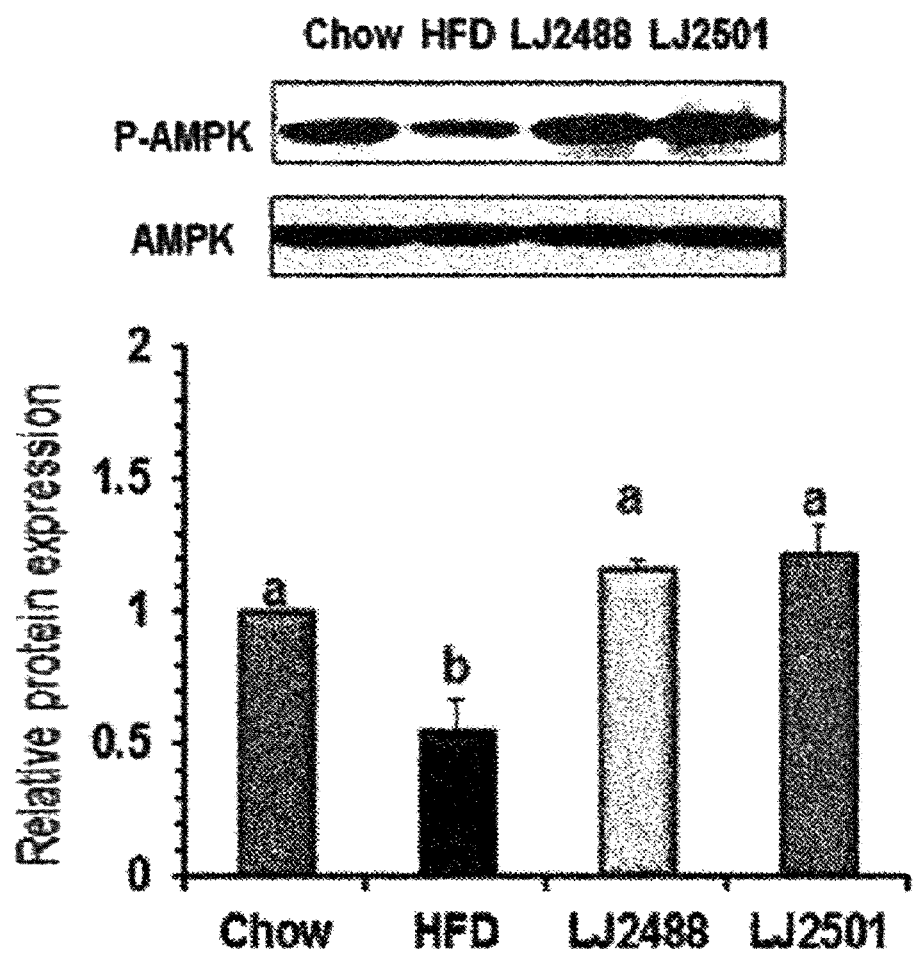

In the liver tissue, the LXRα (liver receptor Xα)-SREBP1c signaling pathway has been known as a major pathway causing fatty liver. LXRα, as a nuclear transcription factor, which regulates lipogenesis with SREBP-1c in the liver tissue, regulates the expression of lipogenesis genes, such as LPL (lipoprotein lipase), FAS, ACC (acetyl-CoA carboxylase), etc. Activated AMPK (AMP-activated protein kinase) inhibits the promoter activity of LXRα, whereby fatty liver is improved. In mice fed HFD diets, the phosphorylation of AMPK was significantly reduced compared with the Chow group, and the expression levels of lipogenesis genes, such as LXRα, SREBP-1c, LPL, FAS, ACC, etc., were significantly increased. Additionally, LJ2501 diets reversed the effects caused by HFD diets, including a reduction of AMPK phosphorylation and an increase of the expression of downstream genes of AMPK, and thus the LJ2501 group exhibited similar expression patterns for AMPK and target genes thereof compared with the Chow group (FIGS. 12A and 12B).

Although the embodiments of the present invention have been disclosed for illustrative purposes, those skilled in the art will appreciate that the embodiments are only preferred embodiments. Accordingly, it is obvious that the scope of the present invention is not limited to the embodiment. Therefore, the substantial scope of the present invention will be defined by the accompanying claims and equivalents thereof.

The invention claimed is:

1. A pentadienoyl piperidine derivative represented by Formula 1 below or a pharmaceutically acceptable salt thereof:

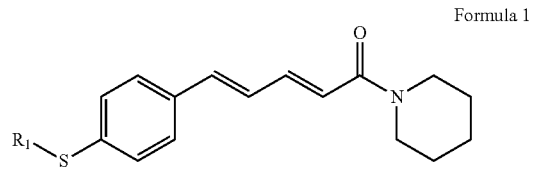

Formula 1 wherein $R_1$ is a $C_1$-$C_3$ alkyl group.

2. The pentadienoyl piperidine derivative or the pharmaceutically acceptable salt thereof according to claim 1, wherein $R_1$ of Formula 1 is a methyl group.

3. A pharmaceutical composition for treatment of metabolic diseases, wherein the pharmaceutical composition comprises the pentadienoyl piperidine derivative or the pharmaceutically acceptable salt thereof according to claim 1 as an active ingredient and the metabolic diseases are selected from the group consisting of obesity, diabetes, dyslipidemia, fatty liver and insulin resistance syndrome.

4. The pharmaceutical composition according to claim 3, wherein the dyslipidemia is hyperlipidemia.

5. The pharmaceutical composition according to claim 3, wherein the fatty liver is non-alcoholic fatty liver.

6. The pharmaceutical composition according to claim 3, wherein the composition reduces the differentiation of adipocytes.

7. The pharmaceutical composition according to claim 3, wherein the composition reduces blood fat, liver fat or visceral fat.

8. The pharmaceutical composition according to claim 7, wherein the visceral fat comprises one or more selected from the group consisting of epididymal fat, perirenal fat, mesenteric fat and retroperitoneal fat.

9. The pharmaceutical composition according to claim 3, the composition reduces the activity of alanine aminotransferase (ALT) or aspartate aminotransferase (AST) in blood.

10. A food composition for improvement or relief of metabolic diseases, wherein the food composition comprises the pentadienoyl piperidine derivative or the pharmaceutically acceptable salt thereof according to claim 1 as an active ingredient and the metabolic diseases are selected from the group consisting of obesity, diabetes, dyslipidemia, fatty liver and insulin resistance syndrome.

11. A method of improving or treating metabolic diseases, wherein the method comprises a step of administrating a composition comprising the pentadienoyl piperidine derivative or the pharmaceutically acceptable salt thereof according to claim 1 as an active ingredient to a subject in need and the metabolic diseases are selected from the group consisting of obesity, diabetes, dyslipidemia, fatty liver and insulin resistance syndrome.

* * * * *